United States Patent
Seo et al.

(10) Patent No.: US 7,226,616 B2
(45) Date of Patent: Jun. 5, 2007

(54) POSITIVELY CHARGED AMPHIPHILIC BLOCK COPOLYMER AS DRUG CARRIER AND COMPLEX THEREOF WITH NEGATIVELY CHARGED DRUG

(75) Inventors: Min-Hyo Seo, Taejeon (KR); In-Ja Choi, Taejeon (KR); Young-Hoon Cho, Taejeon (KR)

(73) Assignee: Samyang Corporation, Seoul (KR)

( * ) Notice: Subject to any disclaimer, the term of this patent is extended or adjusted under 35 U.S.C. 154(b) by 402 days.

(21) Appl. No.: 10/483,826

(22) PCT Filed: Jul. 13, 2002

(86) PCT No.: PCT/KR02/01328

§ 371 (c)(1),
(2), (4) Date: Jan. 14, 2004

(87) PCT Pub. No.: WO03/008480

PCT Pub. Date: Jan. 30, 2003

(65) Prior Publication Data

US 2004/0234494 A1  Nov. 25, 2004

(30) Foreign Application Priority Data

Jul. 14, 2001  (KR) ............................... 2001-42563

(51) Int. Cl.
*A61K 9/14* (2006.01)

(52) U.S. Cl. ...................... 424/486; 424/484; 424/400

(58) Field of Classification Search ................ 424/486, 424/489, 490; 525/542
See application file for complete search history.

(56) References Cited

U.S. PATENT DOCUMENTS

| 4,908,155 A | 3/1990 | Leemans et al. |
|---|---|---|
| 5,035,972 A | 7/1991 | El-Sayed et al. |
| 5,569,448 A | 10/1996 | Wong et al. |
| 5,783,178 A | 7/1998 | Kabanov et al. |
| 5,929,177 A | 7/1999 | Kataoka et al. |
| 5,939,453 A | 8/1999 | Heller et al. |
| 6,201,065 B1 | 3/2001 | Pathak |

FOREIGN PATENT DOCUMENTS

| EP | 0721776 | 1/1996 |
|---|---|---|
| WO | WO 97/10849 A1 | 3/1997 |
| WO | WO 99/18142 A1 | 4/1999 |
| WO | WO 00/18821 A1 | 4/2000 |
| WO | WO0155360 A1 * | 8/2001 |

OTHER PUBLICATIONS

R. Langer—New Methods of Drug Delivery, 249 *Science* 1527-1533 (1990).
B. Jeong, et al,—Biodegradable Block Copolymers as Injectable Drug-delivery Systems, 388 *Nature* 860-862 (1997).

* cited by examiner

*Primary Examiner*—Michael G. Hartley
*Assistant Examiner*—James Rogers, Jr.
(74) *Attorney, Agent, or Firm*—Thorpe North & Western, LLP

(57) ABSTRACT

The present invention provides a cationic group-containing amphiphilic block copolymer that is biocompatible and biodegradable, and when used as a drug carrier for an anionic drug, provides several advantages, such as increased blood concentration and improved stability of the drug.

16 Claims, 14 Drawing Sheets

POSITIVELY CHARGED AMPHIPHILIC BLOCK COPOLYMER AS DRUG CARRIER AND COMPLEX THEREOF WITH NEGATIVELY CHARGED DRUG

This application claims benefit of a patent application filed earlier as PCT International Application No. PCT/KR02/01328, which claims priority to Korean Application No. 2001-42563, filed on Jul. 14, 2001.

BACKGROUND OF THE INVENTION

1. Field of the Invention

The present invention relates to a positively charged drug carrier which forms a complex with a negatively charged drug. More specifically, the present invention relates to a positively charged polymeric micelle type drug carrier which comprises an A-B block type copolymer wherein A is a hydrophilic polymer block and B is a hydrophobic biodegradable polymer block and wherein one end of the hydrophobic polymer block (B) is covalently bound to one cationic group. The positively charged biodegradable block copolymer of the present invention forms a complex with a negatively charged drug via electrostatic interactions. The cationic copolymers of the present invention can be used in drug delivery and are especially useful for delivery of anionic bioactive agents.

2. Related Art

Biodegradable polymers are gaining attention as drug delivery systems. R. Langer, New Methods of Drug Delivery, 249 Science 1527–1533 (1990); B. Jeong et al., Biodegradable Block Copolymers as Injectable Drug-delivery Systems, 388 Nature 860–862 (1997). Delivering bioactive agents from biodegradable delivery systems is very desirable because the need for surgery to remove the delivery system is avoided. Controlled release of bioactive agents can reduce the required frequency of administration by maintaining adequate concentration of the therapeutic agent. One important means of maintaining a proper concentration is to control the degradation rate of the biodegradable drug delivery system.

The biodegradable hydrophobic polymers that are widely used as drug carriers include polylactic acid (PLA), polyglycolic acid (PGA), a copolymer of lactic acid and glycolic acid (PLGA), polycaprolactone (PCL), polyorthoester (POE), polyamino acid (PAA), polyanhydride (PAH), polyphosphazine, polyhydroxybutyric acid (PHB), polydioxanone (PDO), etc. Such polymers have good biocompatibility and the desirable feature of being hydrolyzed and decomposed in a living body to give side products which have no toxicity. For these reasons, they are widely used as drug carriers. In particular, since these polymers are insoluble in water formulations, some drugs can be incorporated into the polymer matrix and then implanted in the body in the form of microspheres, nanospheres, films, sheets, or rods, whereby the drug is slowly released exerting a sustained therapeutic effect. In these types of formulations, the polymers themselves are finally decomposed in the body. However, these polymers have low affinity for water-soluble drugs making it very difficult to incorporate a large amount of drug into the polymer matrix. Even if the drug is effectively incorporated into the polymer matrix, the problem of an initial burst release (referring to the phenomenon whereby a large amount of drug is released within the first few hours) may occur after implantation into the body.

A-B, B-A-B, or A-B-A type block copolymers, wherein A is a hydrophilic polymer block and B is a hydrophobic biodegradable polymer block, have been used as drug carriers for the delivery of physiologically active materials in the form of polymeric micelles, nanospheres, microspheres, gels, etc. These block copolymers have desirable properties such as good biocompatibility and the ability to form core-shell type polymeric micelles in aqueous solutions where the core is composed of hydrophobic blocks and the shell is composed of hydrophilic blocks. Micellar formulations, wherein a poorly water soluble drug can be incorporated into the inside of polymeric micelle to give a micellar solution, are good drug carriers for hydrophobic drugs. However, since the drug is incorporated via hydrophobic interaction between the hydrophobic drugs and hydrophobic polymer, the incorporation efficiency of highly hydrophobic drugs is excellent, but water-soluble hydrophilic drugs are poorly incorporated into those polymeric micelles.

Kataoka et al. (EP 721,776 A1) have developed a method for incorporating a charged water-soluble drug into the inside of a polymeric micelle using a block copolymer consisting of a non-charged block and a charged block. The charged block used by Kataoka is a polyamino acid having an ionic side chain, such as polyaspartic acid, polyglutamic acid, polylysine, polyarginine, or polyhistidine. However, they are not biodegradable in a living body. In addition, since the charged block may include several functional groups having electric charges, when they are combined inside the microsphere via electrostatic binding with a drug having multiple ionic groups, such as peptides or proteins, they may decrease the stability of such drugs.

In view of the foregoing, development of a drug carrier for anionic drug delivery that is biocompatible and biodegradable will be appreciated and desired. Thus, the present invention provides a new type of positively charged amphiphilic block copolymer that is biocompatible and biodegradable and that can effectively deliver the drug without a decrease in its stability. By forming a complex with an anionic drug via electrostatic interaction, the cationic amphiphilic block copolymer of the present invention can effectively incorporate a water-soluble negatively charged drug into the amphiphilic block copolymer. In addition, the block copolymer of the present invention is readily susceptible to metabolic degradation after incorporation and delivery of the drug into the cell.

SUMMARY OF THE INVENTION

The present invention provides a cationic group-containing amphiphilic block copolymer that is biocompatible and biodegradable, and provides for several advantages such as increased blood concentration and improved stability of the drug when used as a drug carrier for an anionic drug. The cationic group-containing amphiphilic block copolymer of the present invention is particularly useful for delivering a drug having multiple anionic groups in the molecule, such as peptide or protein drugs, because it will prevent the drug from being decomposed enzymatically in a living body and will also improve stability of the drug by inhibiting the formation of peptide-peptide or protein-protein complexes.

One aspect of the present invention relates to a block copolymer having the formula:

wherein X represents a cationic group, M represents an anion, A is a biocompatible hydrophilic polymer, B is a biodegradable hydrophobic polymer, and L represents a linker selected from the group consisting of —O—, —NH—, —S— and —COO—.

Another aspect of the present invention relates to a block copolymer having the formula:

wherein X represents a cationic group, M represents an anion, $A^1$ is a biocompatible hydrophilic polymer, B is a biodegradable hydrophobic polymer, L represents a linker selected from the group consisting of —O—, —NH—, —S— and —COO—, wherein said $A^1$ is a member selected from the group consisting of polyalkyleneglycol, polyalkyleneoxide, polyvinylpyrrolidone, polysaccharide, polyacrylamide, polymethacrylamide, polyvinylalcohol and derivatives thereof and said B is a biodegradable polyester.

Another aspect of the present invention relates to a block copolymer having the formula:

$$A^2\text{-}B^1\text{-}L\text{-}X\text{-}M \tag{1c}$$

wherein X represents a cationic group, M represents OH⁻ or an anion, $A^2$ is a biocompatible hydrophilic polymer, $B^1$ is a biodegradable hydrophobic polymer, L represents a linker selected from the group consisting of —O—, —NH—, —S— and —COO—, wherein said $A^2$ is a member selected from the group consisting of polyalkyleneglycol, polyalkyleneoxide, polyvinylpyrrolidone, polysaccharide, polyacrylamide, polymethacrylamide, polyvinylalcohol and derivatives thereof and said $B^1$ is a biodegradable polyester synthesized from monomers selected from the group consisting of D,L-lactide, D-lactide, L-lactide, D,L-lactic acid, D-lactic acid, L-lactic acid, glycolide, glycolic acid, ε-caprolactone, ε-hydroxy hexanoic acid and copolymers thereof.

Another aspect of the present invention relates to a block copolymer having the formula:

$$A^3\text{-}B\text{-}L\text{-}X\text{-}M \tag{1d}$$

wherein X represents a cationic group, M represents an anion, $A^3$ is a biocompatible hydrophilic polymer, B is a biodegradable hydrophobic polymer, L represents a linker selected from the group consisting of —O—, —NH—, —S— and —COO—, and wherein said $A^3$ is a degradable derivative prepared according to the following reaction scheme:

$$nZ+(n-1)Y \rightarrow Z\text{-}(Y\text{-}Z)_{n-2}\text{-}Y\text{-}Z$$

wherein Z represents a water-soluble polymer having a molecular weight of up to 5,000 Daltons, Y represents HOOC—$(CH_2)_m$—COOH or O=C=N—$(CH_2)_m$—N=C=O wherein m is an integer from 0 to 10 and n is an integer from 2 to 100.

The present invention also provides a drug-copolymer complex wherein an anionic drug is combined via electrostatic binding with the cationic amphiphilic block copolymer as explained above. Additional features and advantages of the invention will be apparent from the detailed description that follows, taken in conjunction with the accompanying drawings, which together illustrate, by way of example, features of the invention.

DETAILED DESCRIPTION

Figure 1:
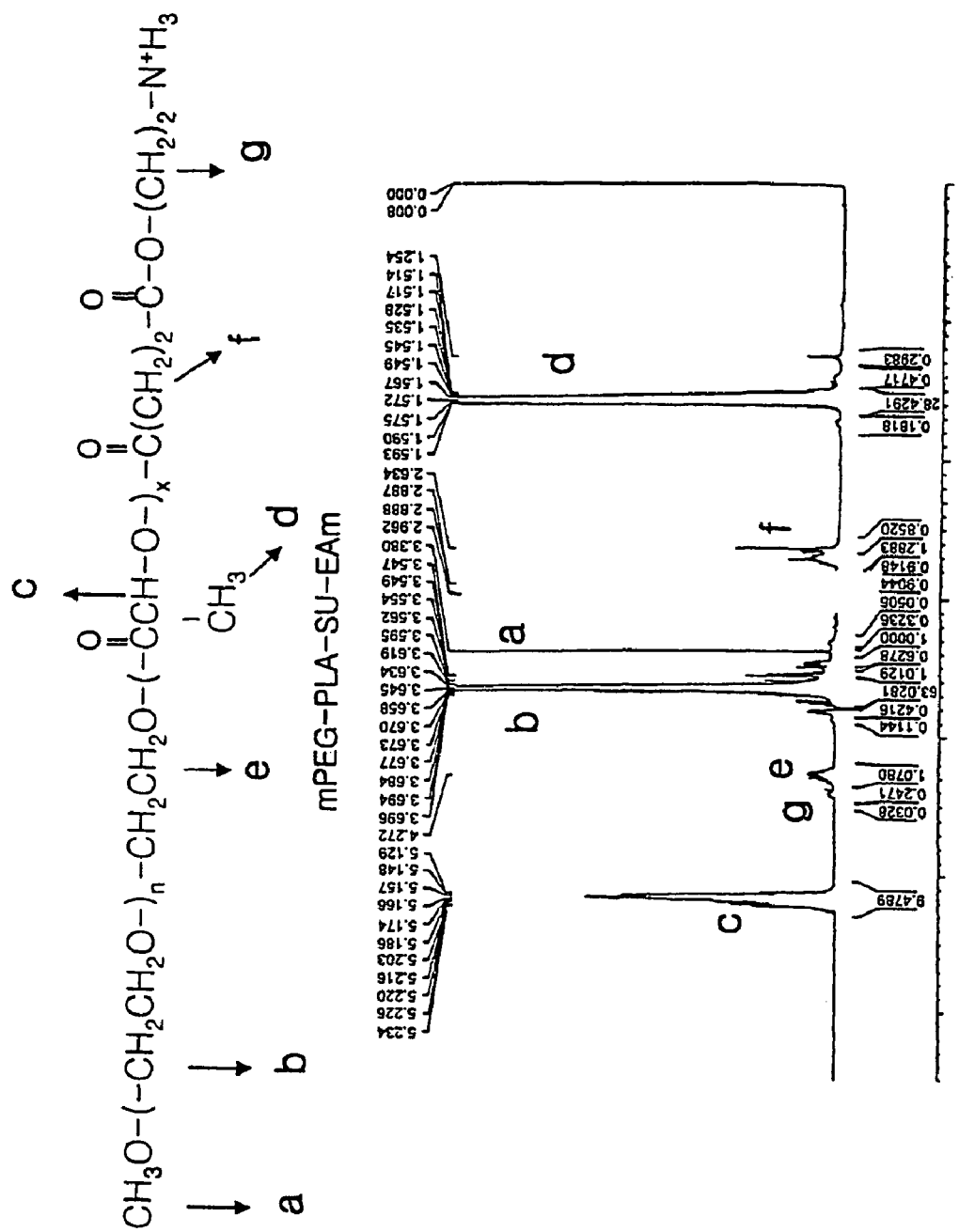
FIG. 1 is an ¹H-NMR(CDCl₃) spectrum of mPEG-PLA-O—C(=O)(CH₂)₂C(=O)—O—CH₂CH₂N⁺H₃.Cl⁻.

Before getting into details of the present composition and method for delivery of a bioactive agent, it should be understood that this invention is not limited to particular configurations, process steps, and materials disclosed herein since such configurations, process steps, and materials may vary to some extent. It should also be understood that the terminology employed herein is used for the purpose of describing particular embodiments only and is not intended to be limited thereby since the scope of the present invention will be limited only by the appended claims and equivalents thereof.

In describing and claiming the present invention, the following terminology will be used in accordance with the definitions set out below.

As used herein, the terms "bioactive agent" or "drug" or any other similar terms mean any chemical or biological material or compound suitable for administration by previously known methods in the art and/or by the methods taught in the present invention and that induce a desired biological or pharmacological effect, which may include but are not limited to (1) having a prophylactic effect on an organism and preventing an undesired biological effect such as infection, (2) alleviating a condition caused by a disease, for example, alleviating pain or inflammation caused as a result of a disease, and/or (3) alleviating, reducing, or completely eliminating a disease from the organism. The effect may be local, such as providing a local anaesthetic effect, or it may be systemic.

As used herein, the term "biodegradable" or "biodegradation" is defined as the conversion of materials into less complex intermediates or end products by solubilization hydrolysis, or by the action of biologically formed entities which can be enzymes and other products of the organism.

As used herein, the term "biocompatible" materials means materials or the intermediates or end products of materials formed by solubilization hydrolysis, or by the action of biologically formed entities which can be enzymes and other products of the organism and which cause no adverse effect to the body.

"Poly(lactide-co-glycolide)" or "PLGA" shall mean a copolymer derived from the condensation copolymerization of lactic acid and glycolic acid, or, by the ring opening polymerization of α-hydroxy acid precursors, such as lactide or glycolide. The terms "lactide," "lactate," "glycolide" and "glycolate" are used interchangeably.

"Poly(lactide)" or "PLA" shall mean a polymer derived from the condensation of lactic acid or by the ring opening polymerization of lactide. The terms "lactide" and "lactate" are used interchangeably.

"Biodegradable polyesters" refers to any biodegradable polyester, which are preferably synthesized from monomers selected from the group consisting of D,L-lactide, D-lactide, L-lactide, D,L-lactic acid, D-lactic acid, L-lactic acid, glycolide, glycolic acid, ε-caprolactone, ε-hydroxy hexanoic acid, γ-butyrolactone, γ-hydroxy butyric acid, δ-valerolactone, δ-hydroxy valeric acid, malic acid, and copolymers thereof.

As used herein, "effective amount" means the amount of a nucleic acid or bioactive agent that is sufficient to provide a desired local or systemic effect and performance at a reasonable risk/benefit ratio as would attend any medical treatment.

As used herein, "peptide" means peptides of any length and includes proteins. The terms "polypeptide" and "oligopeptide" are used herein without any particular intended size limitation, unless a particular size is otherwise stated. Typical peptides that can be utilized are those selected from the group consisting of oxytocin, vasopressin, adrenocorticotrophic hormone, epidermal growth factor, prolactin, luliberin or luteinising hormone releasing hormone, growth hormone, growth hormone releasing factor, insulin, somatostatin, glucagon, interferon, gastrin, tetragastrin, pentagastrin, urogastrone, secretin, calcitonin, enkephalins, endorphins, angiotensins, renin, bradykinin, bacitracins, polymixins, colistins, tyrocidin, gramicidines, synthetic analogues, modifications and pharmacologically active fragments thereof, monoclonal antibodies, and soluble vaccines. The only limitation to the peptide or protein drug which may be utilized is one of functionality.

As used herein, a "derivative" of a carbohydrate includes, for example, an acid form of the sugar, e.g. glucuronic acid; an amine of the sugar, e.g. galactosamine; a phosphate of the sugar, e.g. mannose-6-phosphate; and the like.

As used herein, "administering" and its similar terms mean delivering the composition to an individual being treated so that the composition can be circulated systemically where the composition binds to a target cell and is taken up by endocytosis. Thus, the composition is preferably administered to the individual systemically, typically by subcutaneous, intramuscular, transdermal, oral, transmucosal, intravenous, or intraperitoneal administration. Injectables for such use can be prepared in conventional forms, either a liquid solution or suspension, or a solid form that is suitable for preparation as a solution or suspension in liquid prior to injection, or as an emulsion. Suitable excipients that can be used for administration include, for example, water, saline, dextrose, glycerol, ethanol, and the like; and if desired, minor amounts of auxiliary substances such as wetting or emulsifying agents, buffers, and the like. For oral administration, it can be formulated into various forms such as solutions, tablets, capsules, etc.

Reference will now be made to the exemplary embodiments and specific terms will be used herein to describe the same. It should nevertheless be understood that no limitation of the scope of the present invention is thereby intended. Alterations and further modifications of the inventive features illustrated herein, and additional applications of the principles of the invention as illustrated herein, which one skilled in the relevant art could do and would be aware of after reading this disclosure, are to be considered within the scope of the invention.

The present invention relates to a block copolymer represented by the following formula (1):

$$A\text{-}B\text{-}L\text{-}X\text{-}M \quad (1)$$

wherein X represents a cationic group; M represents an anion, more preferably $OH^-$, $Cl^-$, $Br^-$, $I^-$, $HSO_4^-$, $HCO_3^-$ or $NO_3^-$; A is a biocompatible hydrophilic polymer, B is a biodegradable hydrophobic polymer, and L represents a linker selected from the group consisting of —O—, —NH—, —S—, and —COO—.

The present invention also provides a drug-polymer complex comprising a block copolymer represented by formula (1) and a negatively charged drug wherein the anionic drug is complexed with the cationic amphiphilic block copolymer via electrostatic binding.

The positively charged polymer according to the present invention comprises an A-B amphiphilic block copolymer consisting of hydrophilic blocks (A) and biodegradable hydrophobic blocks (B) wherein one terminal end of the hydrophobic blocks (B) is capped, through a linker, with one cationic group. Examples of the block copolymers include A-B-L-X wherein A is a hydrophilic block, B is a biodegradable hydrophobic block, L is a linker as defined above, and X is a cationic group.

The hydrophilic block (A) is a biocompatible, water-soluble and non-ionic polymer segment which includes a polyalkylene glycol such as polyethylene glycol, poly(ethylene-co-propylene)glycol, polyalkyleneoxide, polyvinylpyrrolidone, a polysaccharide, polyacrylamide, polymethacrylamide, polyvinylalcohol, and derivatives thereof, preferably polyethylene glycol, poly(ethylene-co-propylene)glycol, polyvinylpyrrolidone, polyacrylamide, polyvinylalcohol, and derivatives thereof, and more preferably is polyethyleneglycol and derivatives thereof.

Furthermore, the biocompatible hydrophilic block (A) includes derivatives having a high molecular weight wherein said water-soluble and non-ionic polymer segments having low molecular weights are combined together via degradable linkers. The hydrophilic A block can be synthesized as shown in Reaction Scheme 1:

$$nZ+(n-1)Y \rightarrow Z\text{-}(Y\text{-}Z)_{n-2}\text{-}Y\text{-}Z$$

wherein Z represents a water-soluble polymer having a molecular weight of up to 5,000 Daltons, Y represents $HOOC\text{—}(CH_2)_m\text{—}COOH$ or $O\text{=}C\text{=}N\text{—}(CH_2)_m\text{—}N\text{=}C\text{=}O$ wherein m denotes an integer from 0 to 10, and n denotes an integer from 2 to 100.

The hydrophilic block (A) preferably has a number average molecular weight of 100 to 100,000 Daltons, and may also have any type of structure such as a single chain, a branch, etc. Examples include $PEG\text{-}OOC\text{—}(CH_2)_m\text{—}COO\text{-}PEG$ or $PEG\text{-}[OOC\text{—}(CH_2)_m\text{—}COO\text{-}PEG]_{10}\text{-}OOC\text{—}(CH_2)_m\text{—}COO\text{-}PEG$ wherein the molecular weight of the PEG is up to 5,000 Daltons.

In the positively charged block copolymer according to the present invention, the biodegradable hydrophobic block (B) is preferably a biodegradable polyester synthesized from monomers selected from the group consisting of D,L-lactide, D-lactide, L-lactide, D,L-lactic acid, D-lactic acid, L-lactic acid, glycolide, glycolic acid, ε-caprolactone, ε-hydroxy hexanoic acid, γ-butyrolactone, γ-hydroxy butyric acid, δ-valerolactone, δ-hydroxy valeric acid, malic acid, and copolymers thereof. More preferably, the biodegradable polyester is synthesized from monomers selected from the group consisting of D,L-lactide, D-lactide, L-lactide, D,L-lactic acid, D-lactic acid, L-lactic acid, glycolide, glycolic acid, ε-caprolactone, ε-hydroxy hexanoic acid, and copolymers thereof.

The hydrophobic B-blocks are utilized because of their biodegradable, biocompatible, and solubilization properties. The in vitro and in vivo degradation of these hydrophobic, biodegradable polyester B-blocks are well understood and the degradation products are naturally occurring compounds that are readily metabolized and/or eliminated by a patient's body.

Examples of biodegradable hydrophobic B-blocks include poly(α-hydroxyacid) or derivatives thereof such as polylactic acid (PLA), polyglycolic acid (PGA), a copolymer of lactic acid and glycolic acid (PLGA) and copolymers thereof; polyesters or derivatives thereof such as polyorthoester (POE), polyanhydride (PAH), polycaprolactone (PCL), poly(dioxan-2-one)(PDO), polyhydroxybutyric acid (PHB), a copolymer of lactic acid and dioxan-2-one (PLDO), a copolymer of caprolactone and dioxan-2-one (PCLDO), and copolymers thereof; polyphosphazine; or copolymers thereof. Examples of preferred biodegradable hydrophobic B polymer blocks include poly(α-hydroxyacid) or derivatives thereof such as hydrolyzable polylactic acid (PLA), polyglycolic acid (PGA), a copolymer of lactic acid and glycolic acid (PLGA), and copolymers thereof; polyester or derivatives thereof such as polyorthoester (POE), polyanhydride (PAH), polycaprolactone (PCL), poly(dioxan-2-one) (PDO), polyhydroxybutyric acid (PHB), a copolymer of lactic acid and dioxan-2-one (PLDO), a copolymer of caprolactone and dioxan-2-one (PCLDO), and copolymers thereof; or copolymers thereof. Examples of more preferred biodegradable hydrophobic B polymer blocks include polylactic acid (PLA), polyglycolic acid (PGA), polycaprolactone (PCL), poly(dioxan-2-one)(PDO), a copolymer of lactic acid and glycolic acid (PLGA), or copolymers thereof.

The hydrophobic block (B) preferably has a number average molecular weight of 100 to 100,000 Daltons, and more preferably 500 to 50,000 Daltons.

The cationic group (X) in the positively charged block copolymer, according to the present invention, is attached to the end of the hydrophobic block (B) by means of a linker L.

If the terminal end of the hydrophobic block (B) is a functional —OH, —NH$_2$, —SH or —COOH group, the cationic group is directly linked to the hydrophobic block (B) with the functional group providing the linker L. If not, the hydrophobic B block can be derivatized so that it can be linked to the cationic group through a suitable linker (L), such as, —O—, —NH—, —S— or —COO—. In the present invention, only one cationic group (X) can be present at the end of B hydrophobic polymer block. The cationic group is selected from those that are positively charged in aqueous solutions, preferably —C(=O)—(CH$_2$)$_z$—(C=O)—O—CH$_2$CH$_2$—Y or —C(=O)CHR$^1$Y wherein R$^1$ represents H, a methyl, benzyl, 2-methylpropyl, or 1-methylpropyl group, Y represents —NH$_3^+$, —NRH$_2^+$, —NR$_2$H$^+$, or —NR$_3^+$ wherein R represents a methyl, ethyl or 2-hydroxyethyl group, and z denotes an integer from 0 to 6.

Therefore, one embodiment of the positively charged block copolymer according to the present invention can be represented by the following formula 1a:

A-B-L-X'M (1a)

wherein A is a biocompatible hydrophilic polymer block; B is a biodegradable hydrophobic polymer block; L is a linker selected from the group consisting of —O—, —NH—, —S—, and COO—, X$^1$ is —C(=O)—(CH$_2$)$_z$—(C=O)—O—CH$_2$CH$_2$—Y, and —C(=O)CHR$^1$Y wherein Y is —NH$_3^+$, —NRH$_2^+$, —NR$_2$H$^+$, or —NR$_3^+$, R is a methyl, ethyl or 2-hydroxyethyl group, R$^1$ is H, a methyl, benzyl, 2-methylpropyl or 1-methylpropyl group, and z denotes an integer from 0 to 6; and M is an anion, preferably OH$^-$, Cl$^-$, Br$^-$, I$^-$, HSO$_4^-$, HCO$_3^-$ or NO$_3^-$.

More specifically, the positively charged block copolymer of the present invention may have the following formula:

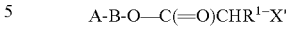

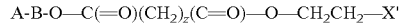

wherein A is a member selected from the group consisting of methoxypolyethyleneglycol, polyethyleneglycol, polyvinylpyrrolidone, polyacrylamide, poly(ethylene-co-propylene)glycol, polyvinylalcohol or polysaccharide; B is a member selected from the group consisting of polylactide, polyglycolide, polycaprolactone, poly(dioxan-2-one), polyanhydride, poly(lactic-co-glycolide), poly(lactic-co-caprolactone) and poly (lactic-co-dioxan-2-one); X' is —NH$_3^+$Cl$^-$, —NRH$_2$+Cl$^-$, —NR$_2$H+Cl$^-$, or —NR$_3^+$Cl$^-$ wherein R is a methyl, ethyl or 2-hydroxyethylgroup; R$^1$ is H, a methyl, benzyl, 2-methylpropyl or 1-methylpropyl group, and z denotes an integer from 0 to 6.

The positively charged block copolymer of the present invention is prepared by a two-step reaction which comprises synthesizing A-B block type copolymers consisting of non-ionic hydrophilic blocks (A) and hydrophobic blocks (B), and then introducing a cationic group onto the terminal end of an appropriately derivatized hydrophobic block (B).

1) Introduction of Amino Acid Groups

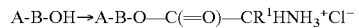

In the above scheme, and with reference to formula 1, L is —O—, X is C(=O)—CR$^1$HNH$_3^+$, M is Cl$^-$ and R$^1$ is H, a methyl, benzyl, 2-methylpropryl or 1-methylpropyl group.

A-B block type copolymers are reacted with an amino acid derivative bearing a protection group on the amino group wherein the protection group is removed after the reaction, is then treated with an aqueous acidic solution, neutralized, dialyzed, and then lyophilized. The order of neutralization and dialysis may be reversed depending on the reagent used.

2) Introduction of Aminoethyl Groups

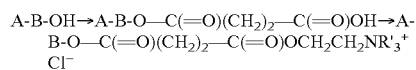

In the above scheme, and with reference to formula 1, L is —O—, X is C(=O)(CH$_2$)$_2$—C(=O)OCH$_2$CH$_2$NR'$_3^+$, M is Cl$^-$0 and R' is H, a methyl, ethyl or 2-hydroxyethyl group.

A-B block type copolymers are reacted with succinyl dichloride or succinyl anhydride to give A-B block type copolymers containing a terminal carboxylic group, condensed with aminoethanol chloride, monomethyl aminoethanol chloride, dimethyl aminoethanol chloride, or choline chloride bearing a protection group on the amino group wherein the protection group is removed after the reaction, then treated with an aqueous acidic solution, neutralized, dialyzed, and then lyophilized.

The positively charged block copolymer of the present invention may form a polymeric micelle, nanoparticle or gel by incorporating the water-soluble drug, having an anionic group, into the inside of the core of the core-shell type drug carrier via electrostatic binding, and whereby the concentration in blood of the drug may be increased. Furthermore, peptide or protein drugs may be combined with the positively charged block copolymer of the present invention via electrostatic binding in the form of one peptide or protein molecule being surrounded by several block copolymers. In this case, decomposition of the peptide or protein by enzymatic action in a living body may be prevented, and the stability of the drug may be improved by the prevention of the formation complexes between protein-protein or peptide-peptide. The release rate of drug from the positively charged block copolymer of the present invention may be controlled by adjusting the molecular weight of the hydrophobic block (B).

The drug-copolymer complex of the present invention should be understood to include such forms as polymeric micelles, nanoparticles, gels, etc. wherein the cationic group of the positively charged block copolymer is electrostatically combined with the anionic group of the negatively charged drug to form an ionic complex, which is to be converted into the aforementioned forms in an aqueous solution. One or more of the positively charged block copolymer is combined with one molecule of drug in the drug-copolymer complex. This type of drug-copolymer complex may increase the concentration and half life of the drug in the blood stream, improve stability of an unstable drug, and retard enzymatic decomposition of the drug in a living body, particularly peptide or protein drugs. If a drug contains a large number of anionic groups in the molecule, such as peptide or protein drugs do, several block copolymer molecules are electrostatically combined with the drug molecule, whereby the formation of complexes between drugs is prevented, and thus stability of the drug is improved.

Drugs that can be used in the present invention include those having anionic groups in aqueous solutions, particularly those having at least one carboxylic, phosphate or sulfate group. Preferably peptides, proteins or enzymes having at least one carboxylic group can be used. Examples include anti-cancer agents, antibiotics, anti-emetic agents, antiviral agents, anti-inflammatory and analgesic agents, anesthetic agents, anti-ulceratives, agents for treating hypertension, agents for treating hypercalcemia, agents for treating hyperlipidemia, etc., each of which has at least one carboxylic, phosphate or sulfate group in the molecule, preferably peptides, proteins or enzymes such as insulin, calcitonin, growth hormone, granulocyte colony-stimulating factor (G-CSF), erythropoietin (EPO), bone morphogenic protein (BMP), interferon, interleukin, platelet derived growth factor (PDGF), vascular endothelial growth factor (VEGF), fibroblast growth factor (FGF), nerve growth factor (NGF), urokinase, etc., each of which has at least one carboxylic, phosphate or sulfate group in the molecule.

In the process for preparation of the drug-block copolymer complex of the present invention, the drug may be incorporated into the inside of the block copolymer by way of simply mixing the negatively charged drug with the positively charged block copolymer in an aqueous solution; or by dissolving the negatively charged drug and the positively charged block copolymer in an organic solvent such as ethanol, etc., evaporating the solvent, and dissolving the resulting mixture in an aqueous solution. As stated above, it is another characteristic of the present invention that a special method is not required for incorporating the negatively charged drug into the inside of the positively charged block copolymer.

The drug-block copolymer complex according to the present invention can be administered through blood, muscle, subcutaneous tissue, bone, or local tissue, or administered orally or nasally. It can be formulated into various forms such as solutions, injectables, suspensions, tablets, capsules, etc.

The following examples will enable those skilled in the art to more clearly understand how to practice the present invention. It is to be understood that, while the invention has been described in conjunction with the preferred specific embodiments thereof, the following is intended to illustrate and not to limit the scope of the invention. Other aspects of the invention will be apparent to those skilled in the art to which the invention pertains.

EXAMPLES

The following preparations illustrate the synthesis of A-B block type copolymers consisting of a hydrophilic polymer segment (A) and a hydrophobic polymer segment (B).

Preparation 1: Synthesis of monomethoxypolyethyleneglycol-polylactide (mPEG-PLA) block copolymers 5.0 g of monomethoxypolyethyleneglycol (Molecular weight: 2,000 Daltons) was introduced into a two-neck 100 ml round-bottomed flask, and heated to 100° C. for 2–3 hours under reduced pressure (1 mmHg) to remove any moisture. The inside of the reaction flask was filled with dry nitrogen and then the catalyst, stannous octoate($Sn(Oct)_2$) dissolved in toluene, was added in the amount of 1.0 mol % (10.13 mg, 0.025 mmole) with respect to the monomethoxypolyethyleneglycol. After stirring for 30 minutes, the mixture was heated to 110° C. for 1 hour under reduced pressure (1 mmHg) to evaporate the toluene which was used to dissolve the catalyst. 5 g of purified lactide was added thereto and the resulting mixture was heated to 130° C. for 12 hours. The block copolymer thus produced was dissolved in ethanol and then added to diethylether to precipitate the block copolymer. The block copolymer thus obtained was dried for 48 hours in a vacuum oven. The molecular weight of the resulting block copolymer (mPEG-PLA) was measured 2000(PEG)–1,765(PLA) Daltons.

Preparation 2: Synthesis of monomethoxypolyethyleneglycol-poly(lactic-co-glycolide)(mPEG-PLGA) block copolymers 5.0 g of monomethoxypolyethyleneglycol (Molecular weight: 5,000 Daltons) was reacted with 3.72 g of lactide and 1.28 g of glycolide in the presence of stannous octoate at 130° C. for 6–12 hours according to the same manner as in Preparation 1, to give the title block copolymer. The molecular weight of the resulting block copolymer (mPEG-PLGA) was measured as 5000(PEG)–4,500(PLGA) Daltons.

Preparation 3: Synthesis of monomethoxypolyethyleneglycol-poly(lactic-co-paradioxan-2-one)(mPEG-PLDO) block copolymers 10.0 g of monomethoxypolyethyleneglycol (Molecular weight: 12,000 Dalton) was reacted with 3.45 g of lactide and 1.05 g of paradioxan-2-one in the presence of stannous octoate at 110° C. for 12 hours according to the same manner as in Preparation 1, to give the title block copolymer. The molecular weight of the resulting block copolymer (mPEG-PLDO) was measured as 12,000–5,400 Daltons.

Preparation 4: Synthesis of monomethoxypolyethyleneglycol-polycaprolactone (mPEG-PCL) block copolymers 7.0 g of monomethoxypolyethyleneglycol (Molecular weight: 12,000 Dalton) was reacted with 3.0 g of ε-caprolactone in the presence of stannous octoate at 130° C. for 12 hours according to the same manner as in Preparation 1, to give the title block copolymer. The molecular weight of the resulting block copolymer (mpEG-PCL) was measured as 12,000–5,000 Daltons.

Table 1 is a summary of the results of the above preparations.

| Preparation | Block copolymer | Number Average Molecular Weight (Daltons) |
| --- | --- | --- |
| 1 | mPEG-PLA-OH | 2,000–1,765 |
| 2 | mPEG-PLGA-OH | 5,000–4,500 |
| 3 | mPEG-PLDO-OH | 12,000–5,400 |
| 4 | mPEG-PCL-OH | 12,000–5,000 |

The following examples illustrate synthesis of A-B block type copolymers containing a cationic group.

Example 1

Synthesis of methoxypolyethyleneglycol-polylactide Containing Amino Group(—O—C(=O)CHR$^1$—NH$_3^+$Cl$^-$), i.e. (mPEG-PLA-O—C(=O)CHR$^1$—NH$_3^+$—Cl$^-$)

The block copolymer synthesized in preparation 1, and having an —OH group at the terminal end of the PLA (hydrophobic B) block, was reacted with an amino acid derivative bearing a protecting group on the amino group to give the title block copolymer.

mPEG-PLA-OH+BzOC(=O)NHCHR$^1$C(=O)OH→mPEG-PLA-O—C(=O)CHR$^1$NHC(=O)OBz→mPEG-PLA-O—C(=O)CHR$^1$NH$_3^+$.Cl$^-$ 0.583 g of N-benzyloxycarbonyglycine, 0.575 g of dicyclohexyl carbodiimide (DCC) and 7.0 g of methoxypolyethyleneglycol-polylactide (mPEG-PLA, 2,000–1,765) were dissolved in 20 ml of DMF. The resulting solution was reacted at room temperature for 24 hours to give N-benzyloxycarbonylglycin methoxypolyethyleneglycol-polylactide ester. The reaction product was hydrogenized using palladium as a catalyst to remove the protection group on the amino group, then dissolved in an aqueous hydrochloride solution, dialyzed, and then lyophilized to give 6.19 g of the title block copolymer.

Examples 2 to 4

Introduction of an Amino Acid Group

Each of the block copolymers synthesized in Preparations 2 to 4 was reacted with an amino acid derivative bearing a protection group on the amino group according to the same manner as in Example 1, giving copolymers containing an amino acid group. The block copolymers containing an amino acid group as prepared in Examples 1 to 4 are represented in the following Table 2.

TABLE 2

| Ex. | Block copolymer | Number Average Molecular Weight (Dalton) | |
|---|---|---|---|
| | | A | B |
| 1 | mPEG-PLA-O—C(=O)CH$_2$—NH$_3^+$—Cl$^-$ | 2,000 | 1,765 |
| 2 | mPEG-PLGA-O—C(=O)CHCH$_3$—NH$_3^+$—Cl$^-$ | 5,000 | 4,500 |
| 3 | mPEG-PLDO—O—C(=O)CH(CH$_2$Ph)—NH$_3^+$—Cl$^-$ | 12,000 | 5,400 |
| 4 | mPEG-PCL-O—C(=O)CH(CH$_2$Ph)—NH$_3^+$—Cl$^-$ | 12,000 | 5,000 |

Example 5

Synthesis of methoxypolyethyleneglycol-polylactide Containing aminoethanol(—O—CH$_2$CH$_2$N$^+$R$_3$—Cl$^-$), i.e. (mPEG-PLA-O—C(=O)(CH$_2$)$_z$C(=O)—O—CH$_2$CH$_2$N$^+$R$_3$—Cl$^-$)

The block copolymer synthesized in Preparation 1 was reacted with dicarboxylic dichloride to give a carboxylic acid derivative. The reaction product was reacted with 2-aminoethanol derivative to give the title block copolymer.

mPEG-PLA-OH+Cl—C(=O)(CH$_2$)$_z$C(=O)—Cl→mPEG-PLA-O—C(=O)(CH$_2$)$_z$C(=O)—Cl→mPEG-PLA-O—C(=O)(CH$_2$)$_z$C(=O)—O—CH$_2$CH$_2$N$^+$R$_3$—Cl$^-$, wherein z denotes an integer from 0 to 6)

7 g of methoxypolyethyleneglycol-polylactide (mPEG-PLA, 2,000–1,765) and 5 g of excess succinyl dichloride were dissolved in chloroform, 1 ml of pyridine was added thereto, and the mixture was reacted at 60° C. for 12 hours. The resulting solution was added to diethylether to precipitate the block copolymer. The precipitated block copolymer was dissolved in 10 ml of N-methylpyrrolidone, 0.363 g of ethanolamime chloride was added thereto, and the mixture was reacted at room temperature for 12 hours. The resulting solution was diluted with distilled water, dialyzed, and then lyophilized to give 5.92 g of the title block copolymer. FIG. 1 is an $^1$H-NMR spectrum (CDCl$_3$) of the block copolymer thus obtained.

Examples 6 to 11

Introduction of an Amino Ethanol Group

Figure 2:
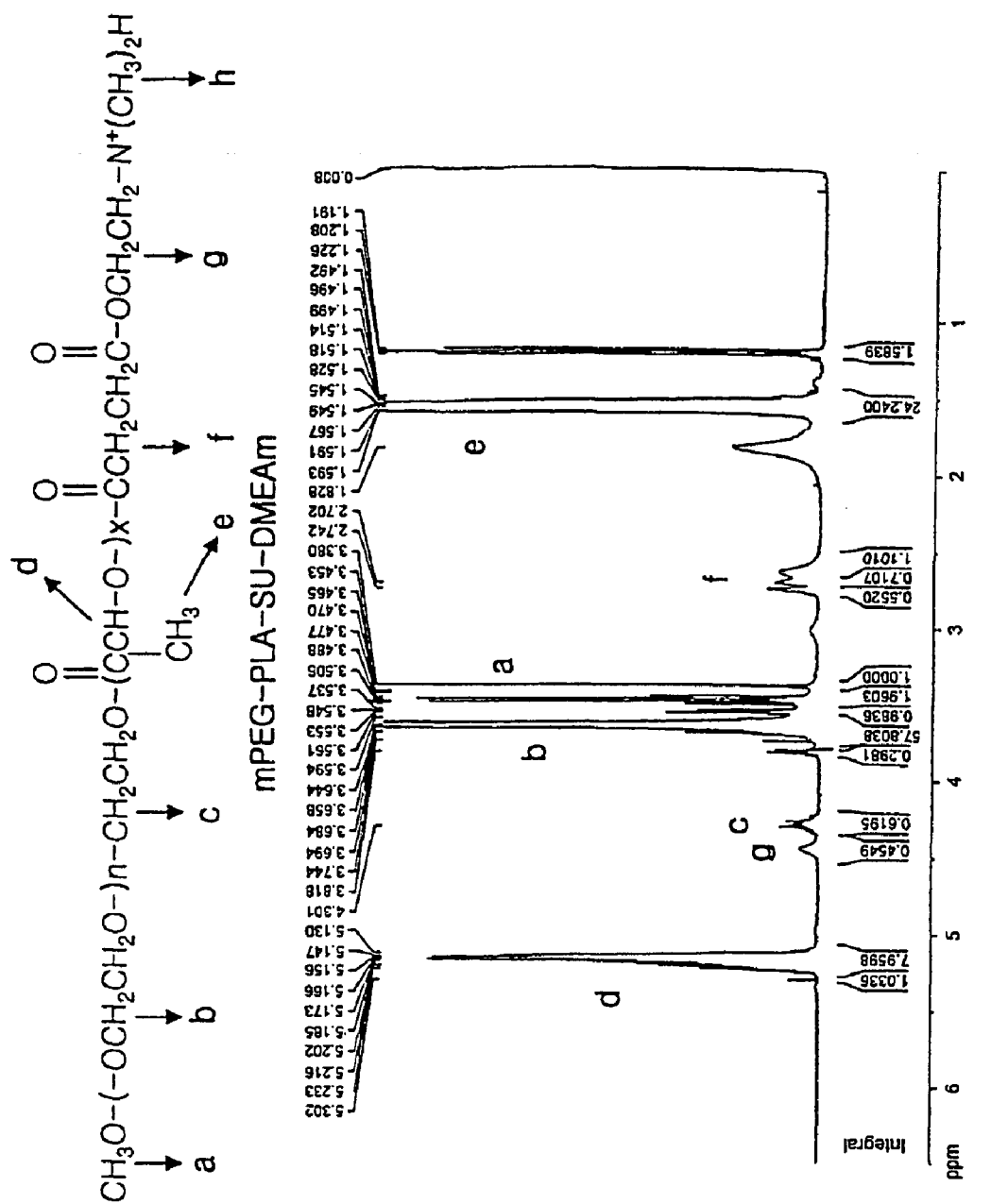
FIG. 2 is an ¹H-NMR(CDCl₃) spectrum of mPEG-PLA-O—C(=O)(CH₂)₂C(=O)—O—CH₂CH₂N⁺(CH₃)₂H.Cl⁻.
Figure 3:
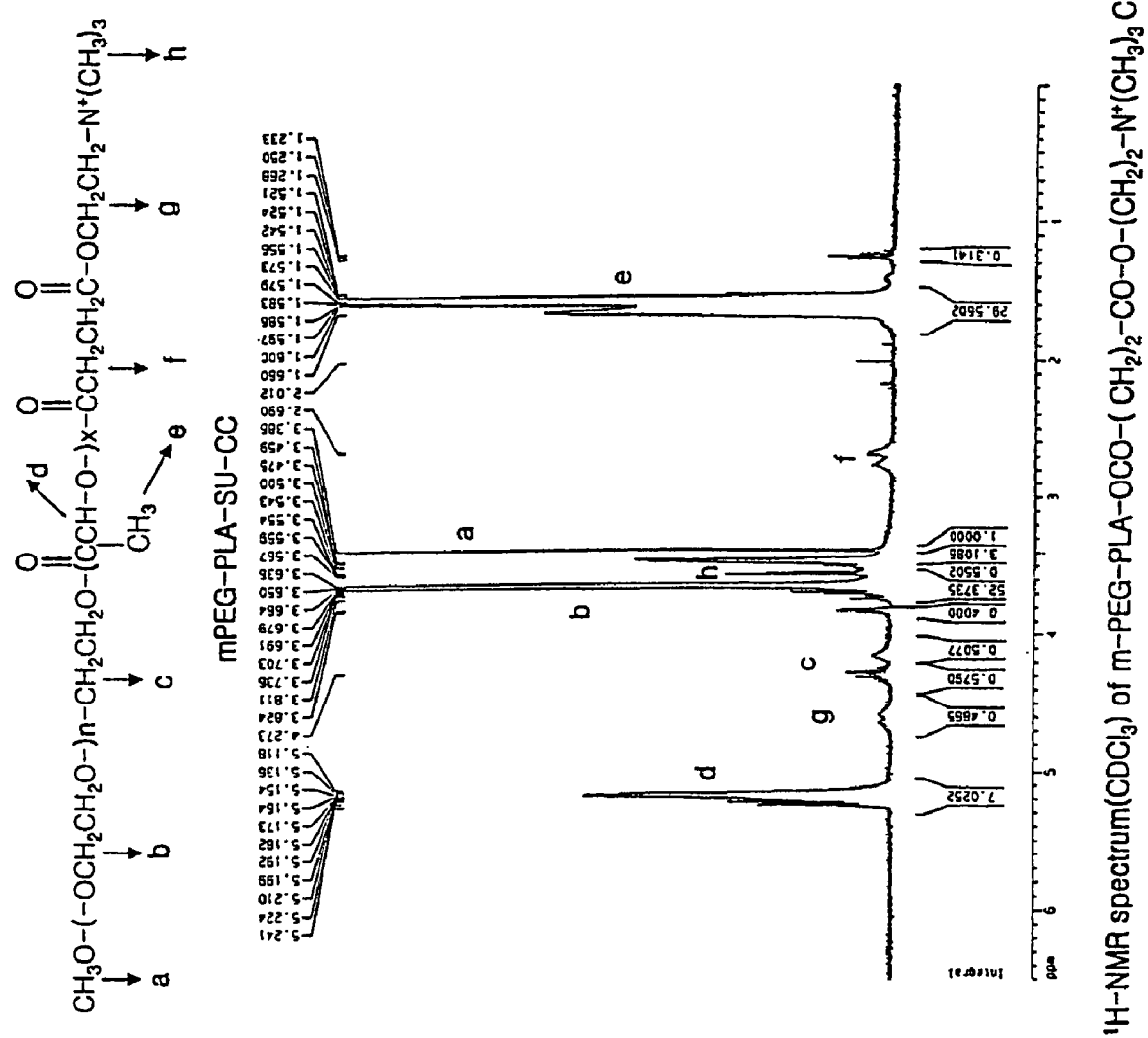
FIG. 3 is an ¹H-NMR(CDCl₃) spectrum of mPEG-PLA-O—C(=O)(CH₂)₂ C(=O)—O—CH₂CH₂N⁺(CH₃)₃.Cl⁻.

Each of the block copolymers prepared in Preparations 1 to 4 was reacted with N-methylaminoethanol chloride, N,N-dimethylaminoethanol chloride or choline chloride according to the same manner as in Example 5 to give copolymers containing an aminoethanol group. The block copolymer as prepared in Examples 5 to 11 are represented in the following Table 3. FIGS. 2 and 3 are $^1$H-NMR spectrums (CDCl$_3$) of the block copolymers of Examples 10 and 11, respectively.

TABLE 3

| Ex. | Block copolymer | Number Average Molecular Weight (Dalton) | |
|---|---|---|---|
| | | A | B |
| 5 | mPEG-PLA-O—C(=O)(CH$_2$)$_2$C(=O)—O—CH$_2$CH$_2$N$^+$H$_3$.Cl$^-$ | 2,000 | 1,765 |
| 6 | mPEG-PLGA-O—C(=O)(CH$_2$)$_3$C(=O)—O—CH$_2$CH$_2$N$^+$(CH$_3$)H$_2$.Cl$^-$ | 5,000 | 4,500 |
| 7 | mPEG-PCL-O—C(=O)(CH$_2$)$_6$C(=O)—O—CH$_2$CH$_2$N$^+$(CH$_3$)$_2$H.Cl$^-$ | 12,000 | 5,000 |
| 8 | mPEG-PLDO—O—C(=O)(CH$_2$)$_2$C(=O)—O—CH$_2$CH$_2$N$^+$(CH$_3$)$_3$.Cl$^-$ | 12,000 | 5,400 |
| 9 | mPEG-PLA-O—C(=O)(CH$_2$)$_2$C(=O)—O—CH$_2$CH$_2$N$^+$(CH$_3$)H$_2$.Cl$^-$ | 2,000 | 1,765 |

TABLE 3-continued

| Ex. | Block copolymer | Number Average Molecular Weight (Dalton) | |
|---|---|---|---|
| | | A | B |
| 10 | mPEG-PLA-O—C(=O)(CH$_2$)$_2$C(=O)—O—CH$_2$CH$_2$N$^+$(CH$_3$)$_2$H.Cl$^-$ | 2,000 | 1,765 |
| 11 | mPEG-PLA-O—C(=O)(CH$_2$)$_2$C(=O)—O—CH$_2$CH$_2$N$^+$(CH$_3$)$_3$.Cl$^-$ | 2,000 | 1,765 |

Example 12

Formation of a diclofenac-Containing mPEG-PLA-O—C(=O)(CH$_2$)$_2$C(=O)—O—CH$_2$CH$_2$N$^+$(CH$_3$)$_3$.Cl$^-$ polymeric micelle mPEG-PLA-O—C(=O)(CH$_2$)$_2$C(=O)—O—CH$_2$CH$_2$N$^+$(CH$_3$)$_3$.Cl$^-$ (10 mg) as prepared in Example 11 and diclofenac (1 mg) were dissolved in distilled water to give the title polymeric micelle.

Example 13

Formation of an indomethacin-Containing mPEG-PLA-O—C(=O)(CH$_2$)$_2$C(=O)—O—CH$_2$CH$_2$N$^+$(CH$_3$)$_2$H.Cl$^-$ polymeric micelle mPEG-PLA-O—C(=O)(CH$_2$)$_2$C(=O)—O—CH$_2$CH$_2$N$^+$(CH$_3$)$_2$H.Cl$^-$ (10 mg) as prepared in Example 10 and indomethacin (1 mg) were dissolved in distilled water to give the title polymeric micelle.

Example 14

Formation of a Complex of Human G-CSF and mPEG-PLA-O—C(=O)(CH$_2$)$_2$C(=O)—O—CH$_2$CH$_2$N$^+$(CH$_3$)$_3$.Cl$^-$ mPEG-PLA-O—C(=O)(CH$_2$)$_2$C(=O)—O—CH$_2$CH$_2$N$^+$(CH$_3$)$_3$.Cl$^-$ (50 mg) as prepared in Example 11 and G-CSF (filgrastim)(1 mg) were dissolved in distilled water to give the title polymeric micelle type-complex.

Example 15

Formation of a Complex of Human Growth Hormone (hGH) and mPEG-PLA-O—C(=O)(CH$_2$C(=O)—O—CH$_2$CH$_2$N$^+$(CH$_3$)$_3$.Cl$^-$ mPEG-PLA-O—C(=O)(CH$_2$)$_2$C(=O)—O—CH$_2$CH$_2$N$^+$(CH$_3$)$_3$.Cl$^-$ (20 mg) as prepared in Example 11 and hGH (1 mg) were dissolved in distilled water to give the title polymeric micelle type-complex.

Figure 12:
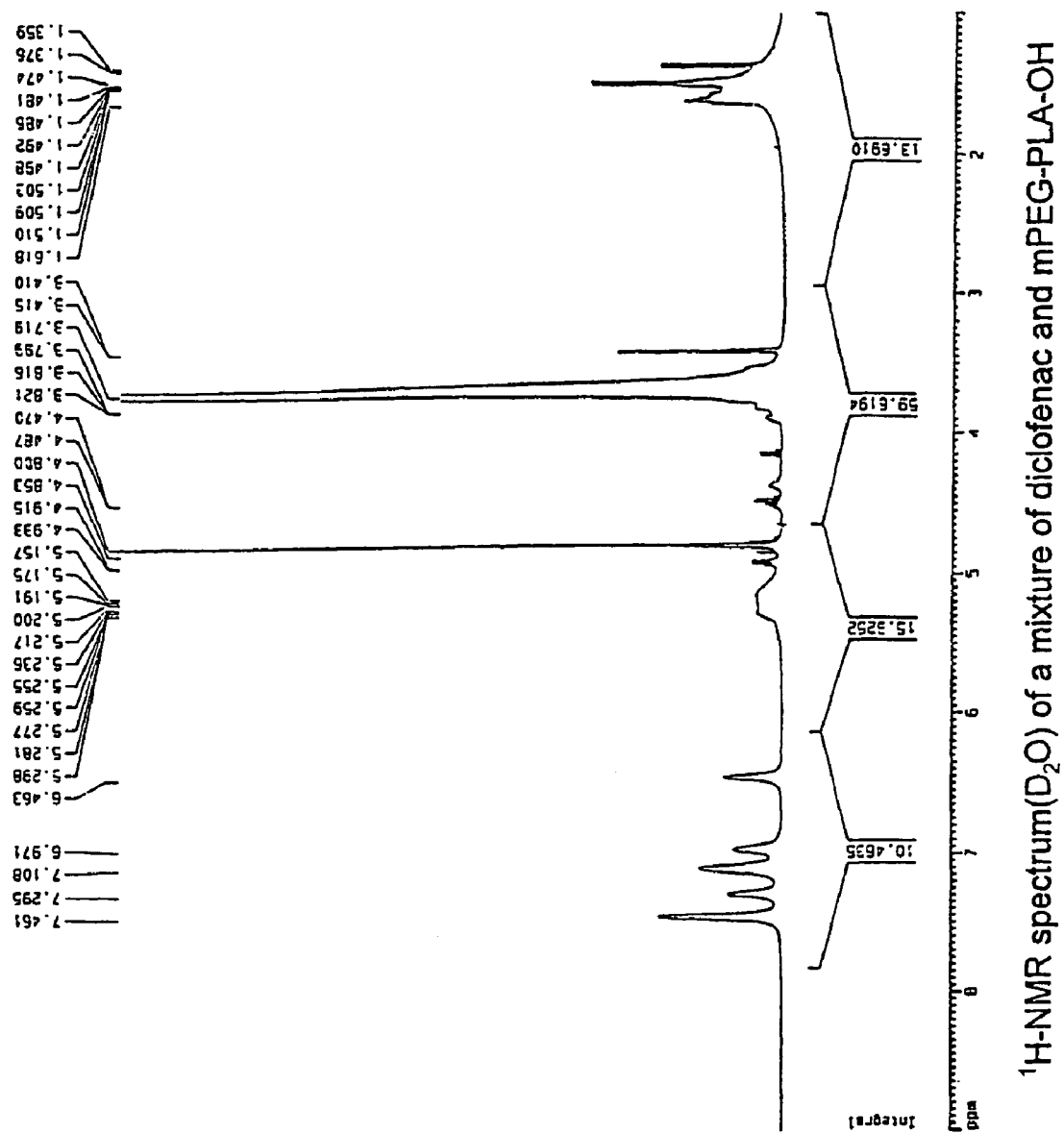
FIG. 12 is an ¹H-NMR(D₂O) spectrum of a mixture of diclofenac and mPEG-PLA-OH.

Comparative Example 1 mPEG-PLA-OH(10 mg) as prepared in Preparation 1, which does not contain a cationic group, and diclofenac (1 mg) were dissolved in distilled water. The aqueous solution obtained was lyophilized, dissolved in D$_2$O, and then analyzed by NMR spectroscopy. The NMR spectrum is represented in FIG. 12.

Experiment 1: Confirmation on whether a Drug-Block Copolymer Complex is Formed

Figure 4:
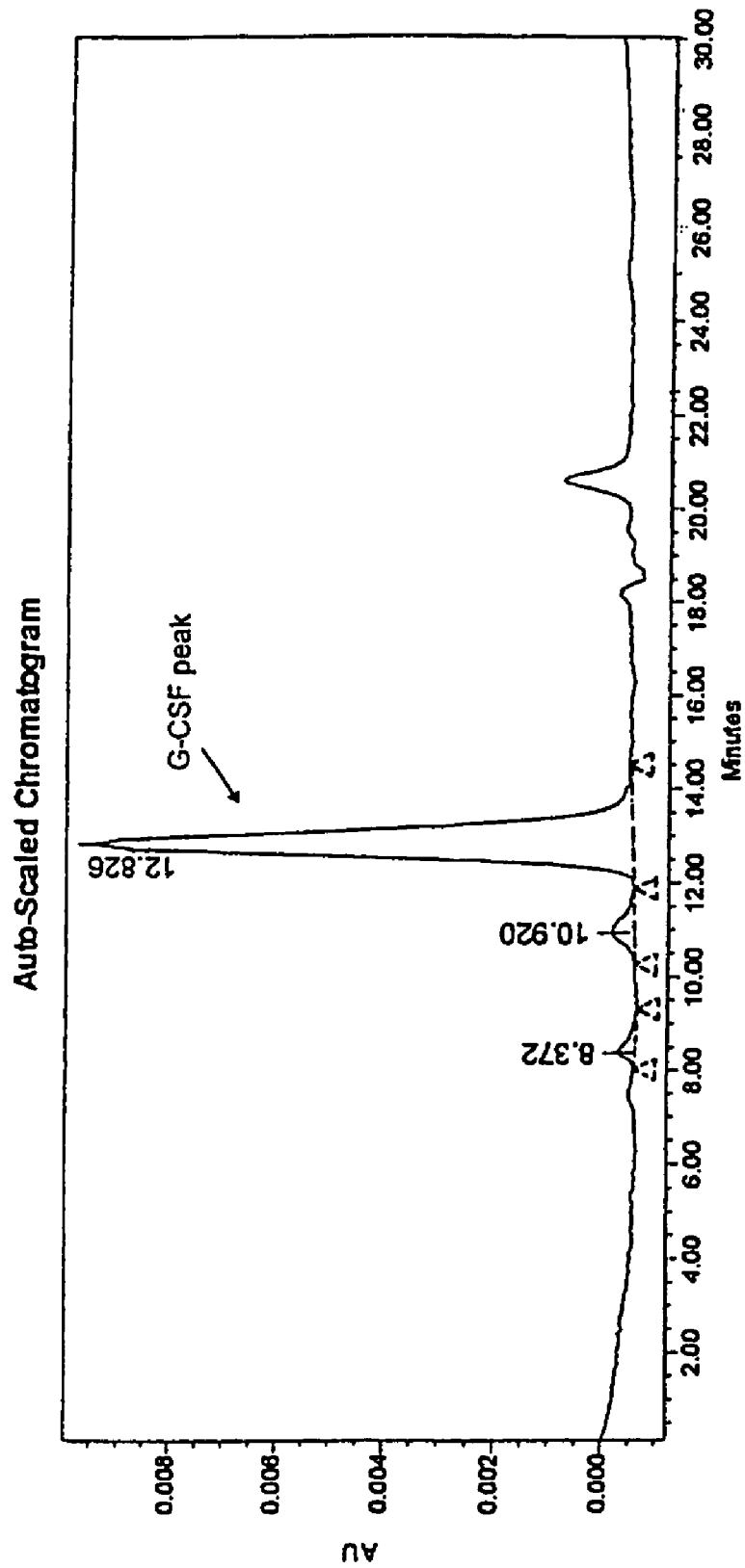
FIG. 4 is a liquid chromatogram of human G-CSF by size exclusive chromatography.
Figure 5:
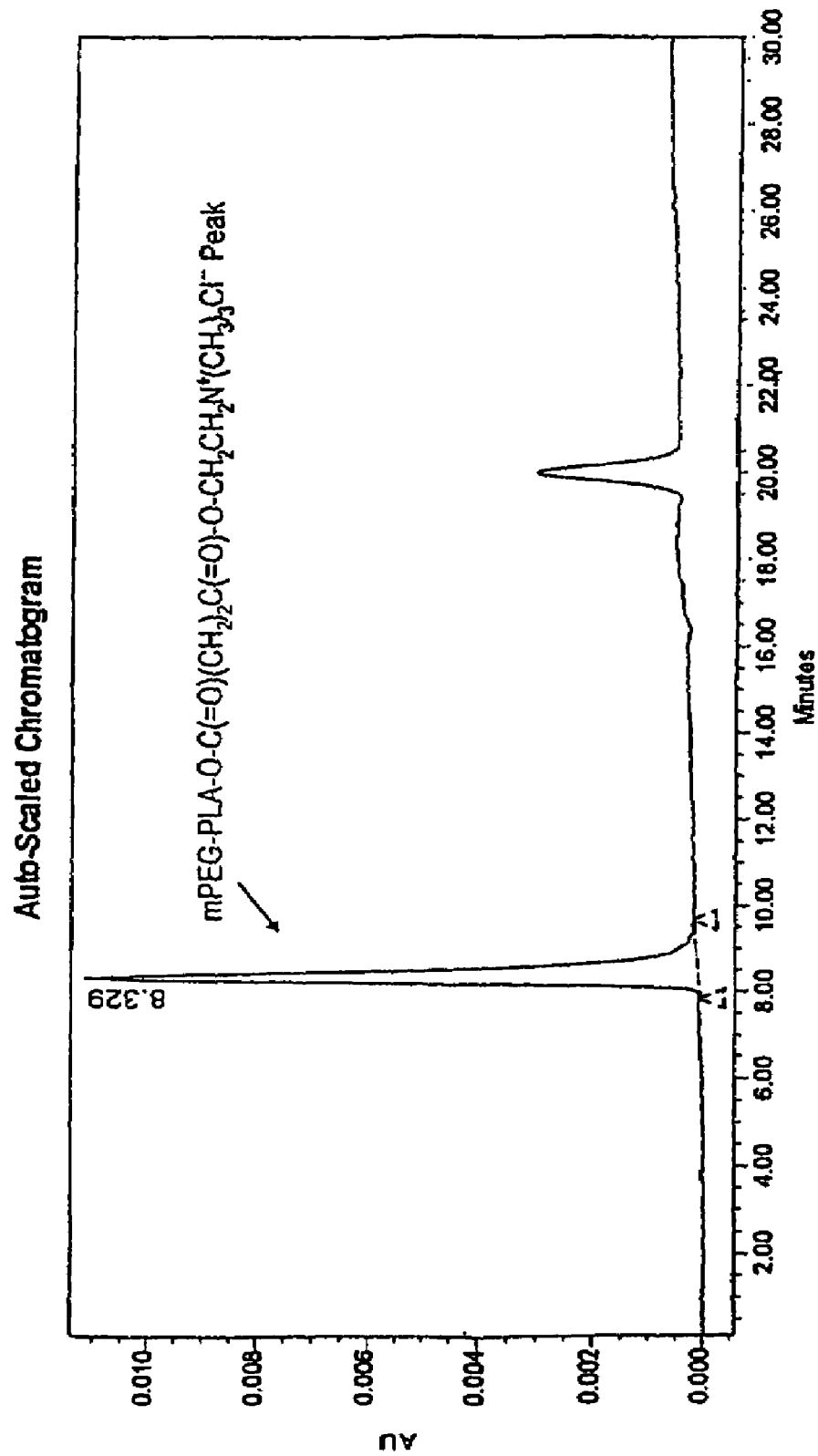
FIG. 5 is a liquid chromatogram of mPEG-PLA-O—C(=O)(CH₂)₂C(=O)—O—CH₂CH₂N⁺(CH₃)₃.Cl⁻ by size exclusive chromatography.
Figure 6:
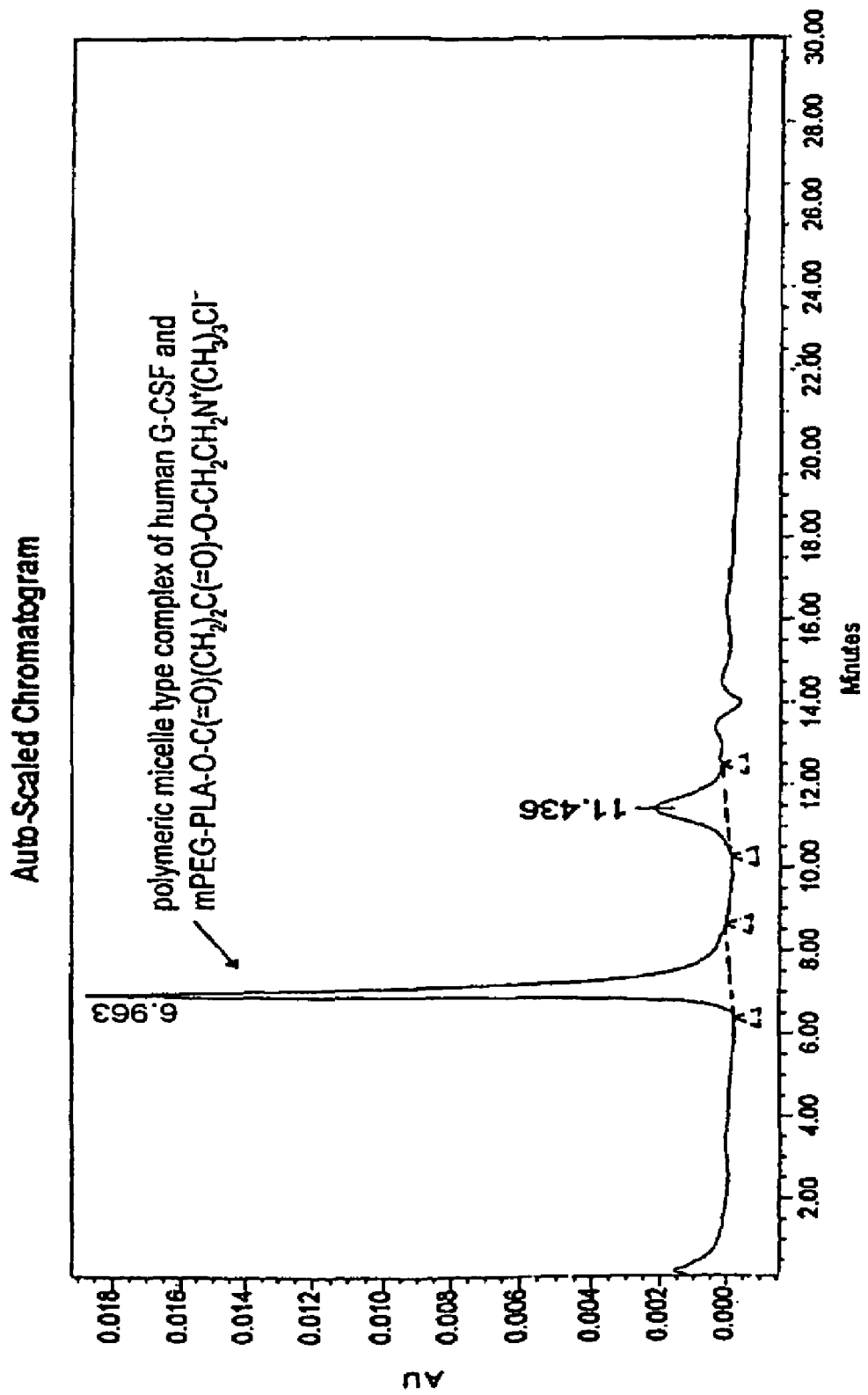
FIG. 6 is a liquid chromatogram of a complex of human G-CSF and mPEG-PLA-O—C(=O)(CH₂)₂C(=O)—O—CH₂CH₂N⁺(CH₃)₃.Cl⁻ by size exclusion chromatography.

Human G-CSF (filgrastim) and mPEG-PLA-O—C(=O)(CH$_2$)$_2$C(=O)—O—CH$_2$CH$_2$N$^+$(CH$_3$)$_3$.Cl$^-$ were analyzed respectively by a size exclusion chromatography column (Pharmacia, Superdex HR 75 10/30) (concentration of human G-CSF: 50 µg/ml, injection amount: 50 microliters, mobile phase: pH 7.4 PBS, flow rate: 1 ml/min). Furthermore, the polymeric micelle solution of Example 14 was analyzed in the same manner. FIGS. 4, 5 and 6 are liquid chromatograms thereof. As can be seen from FIG. 6, G-CSF forms a polymeric micelle type complex with mPEG-PLA-O—C(=O)(CH$_2$)$_2$C(=O)—O—CH$_2$CH$_2$N$^+$(CH$_3$)$_3$.Cl$^-$, and thus the peak corresponding to G-CSF disappears.

Experiment 2: Confirmation on whether a Drug-Block Copolymer Complex is Formed

Figure 7:
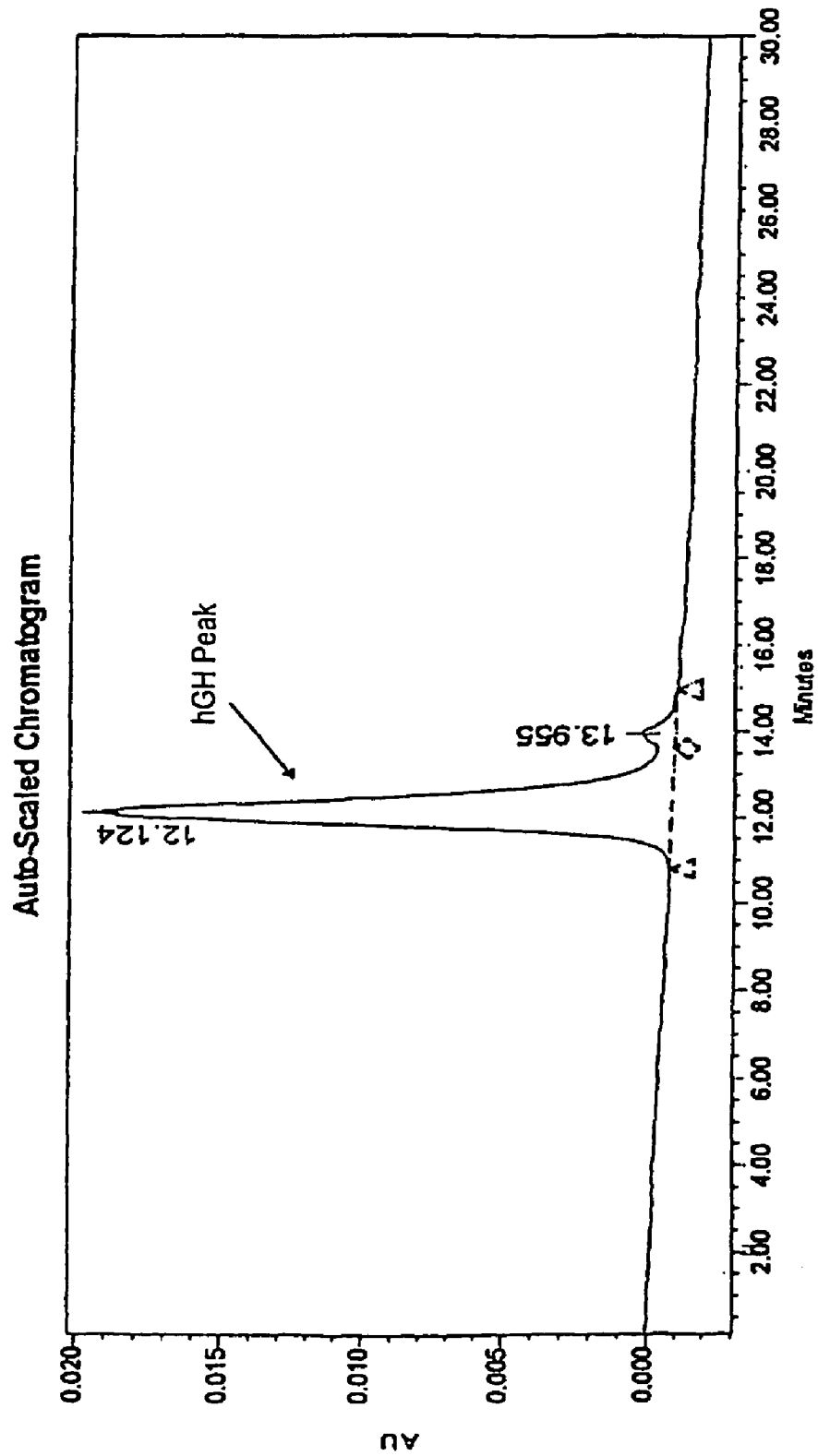
FIG. 7 is a liquid chromatogram of hGH by size exclusion chromatography.
Figure 8:
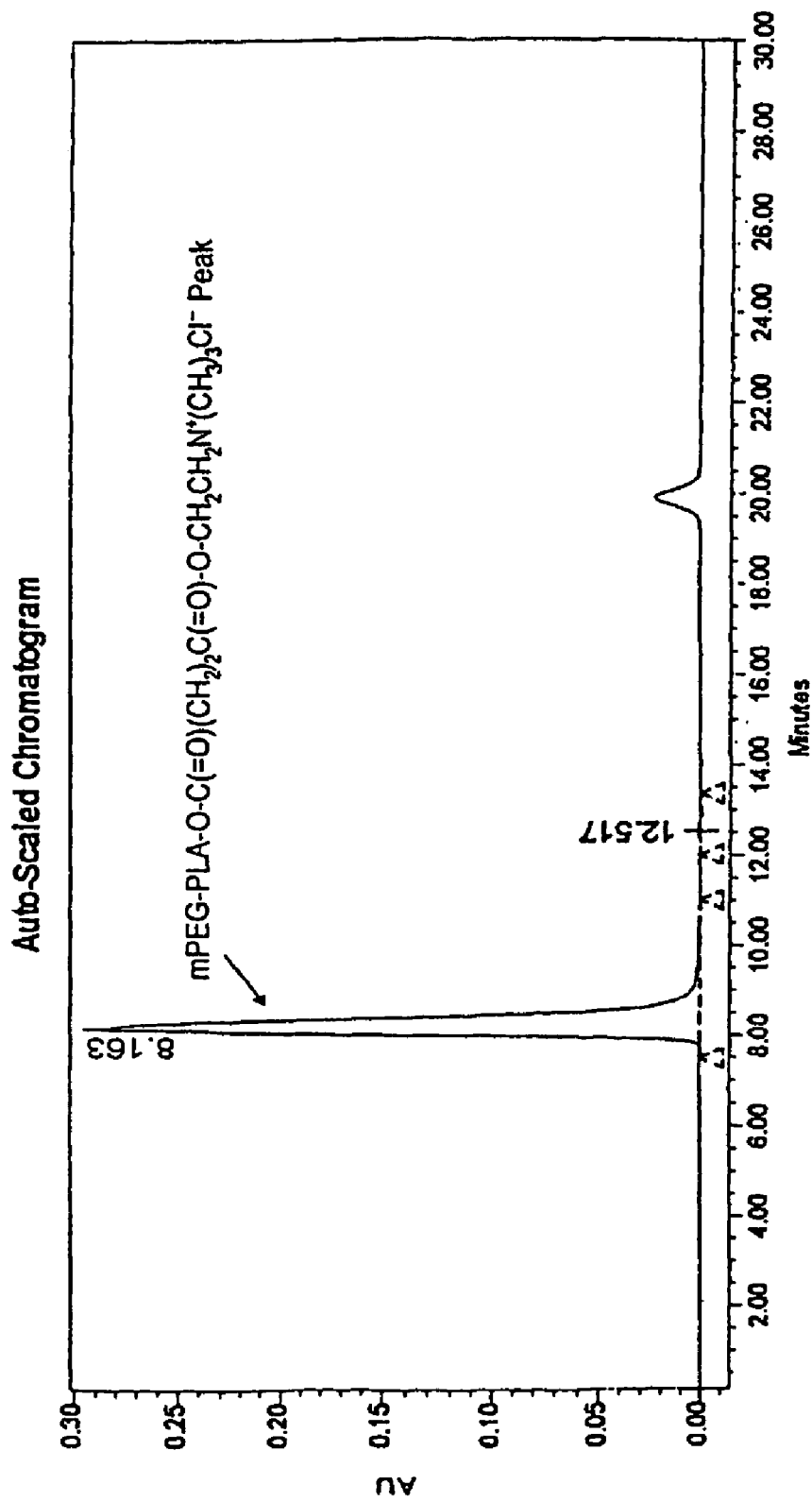
FIG. 8 is a liquid chromatogram of mPEG-PLA-O—C(=O)(CH₂)₂C(=O)—O—CH₂CH₂N⁺(CH₃)₃.Cl⁻ by size exclusion chromatography.
Figure 9:
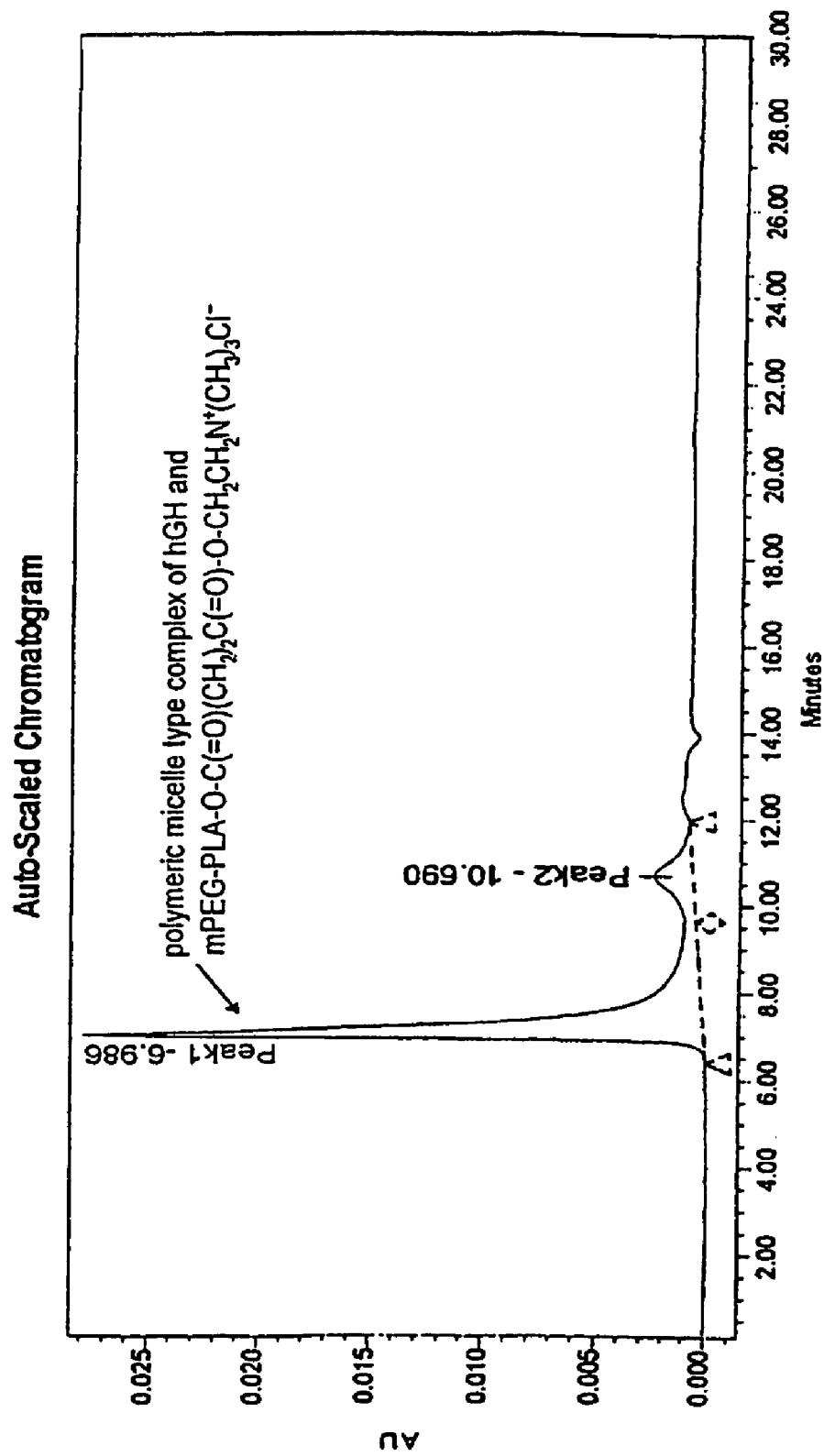
FIG. 9 is a liquid chromatogram of a complex of hGH and mPEG-PLA-O—C(=O)(CH₂)₂C(=O)—O—CH₂CH₂N⁺(CH₃)₃.Cl⁻ by size exclusion chromatography.

Human growth hormone (hGH) and mPEG-PLA-O—C(=O)(CH$_2$)$_2$C(=O)—O—CH$_2$CH$_2$N$^+$(CH$_3$)$_3$.Cl$^-$ were analyzed respectively by a size exclusion chromatography column (Pharmacia, Superdex HR 75 10/30 or Tosoha, TSK gel G3000SW) (concentration of human hGH: 50 µg/ml, injection amount: 100 microliters, mobile phase: pH 7.4 PBS, flow rate: 1 ml/min). Furthermore, the polymeric micelle solution of Example 15 was analyzed according to the same manner. FIGS. 7, 8 and 9 are liquid chromatograms thereof. As can be seen from FIG. 9, hGH forms a polymeric micelle type complex with mPEG-PLA-O—C(=O)(CH$_2$)$_2$C(=O)—O—CH$_2$CH$_2$N$^+$(CH$_3$)$_3$.Cl$^-$, and thus peak corresponding to hGH disappears.

Experiment 3: Confirmation on whether a Drug-Block Copolymer Complex is Formed

Figure 10:
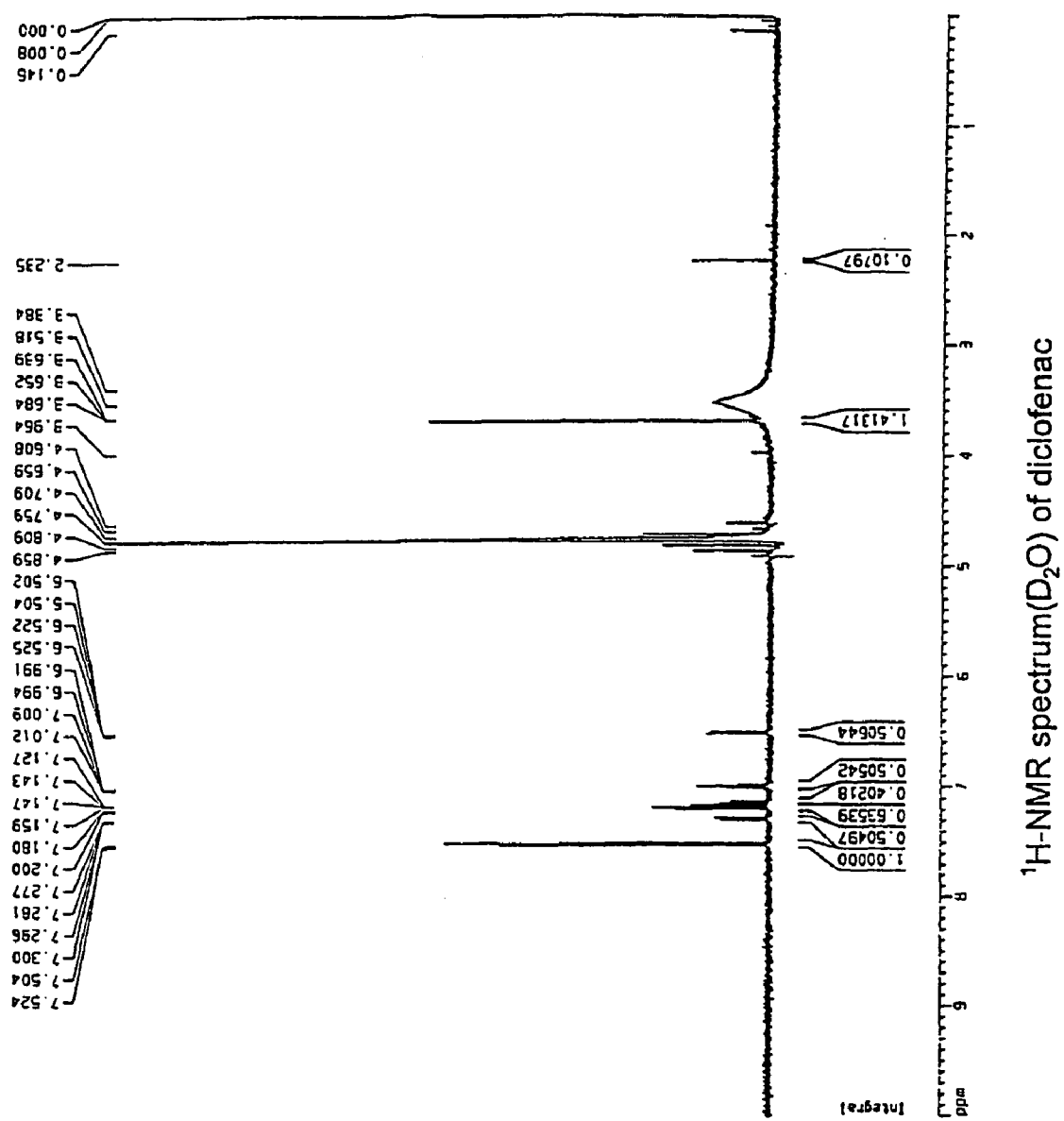
FIG. 10 is an ¹H-NMR(D₂O) spectrum of diclofenac.
Figure 11:
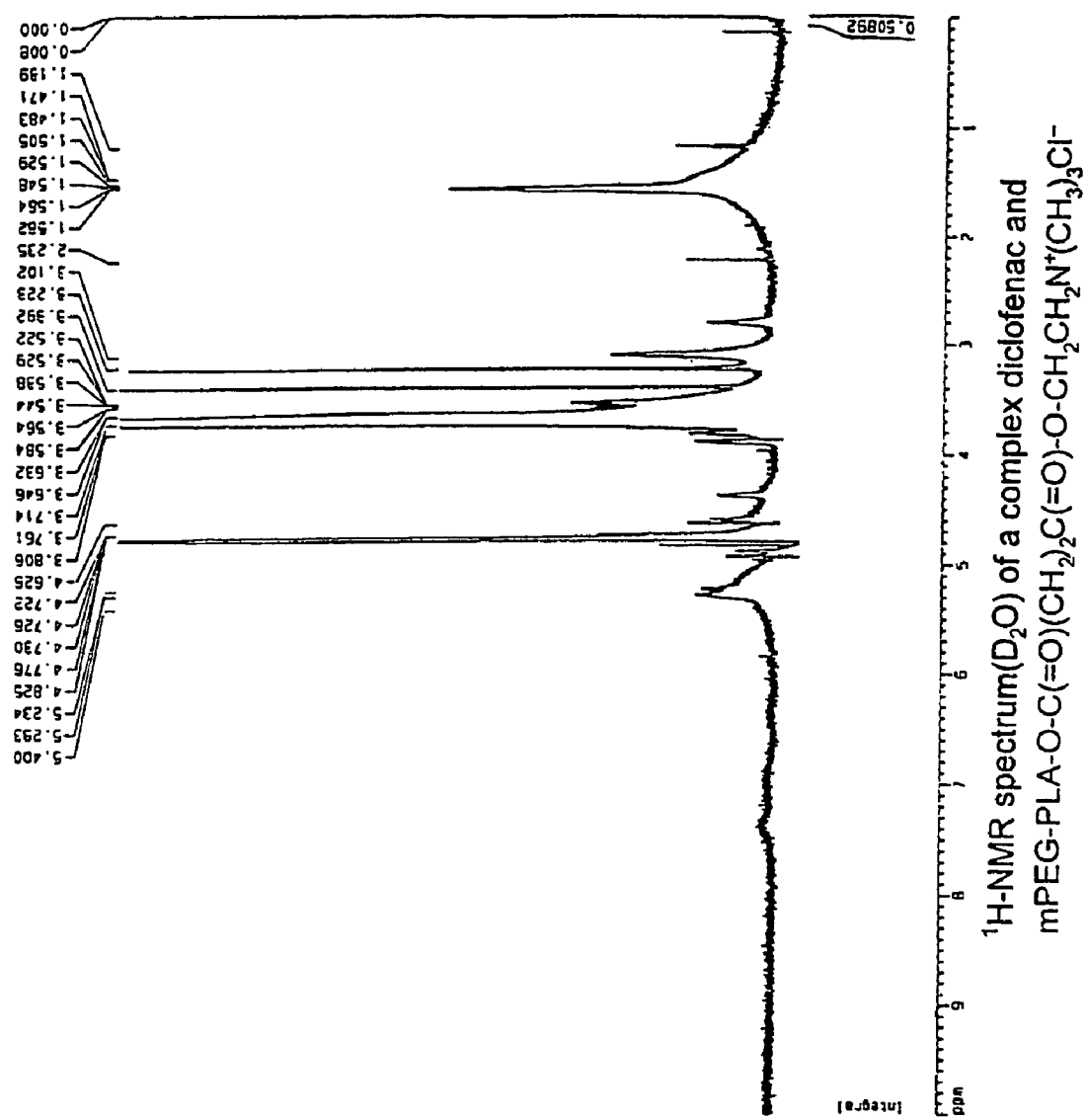
FIG. 11 is an ¹H-NMR(D₂O) spectrum of a complex of diclofenac and mPEG-PLA-O—C(=O)(CH₂)₂C(=O)—O—CH₂CH₂N⁺(CH₃)₃.Cl⁻.

Diclofenac was dissolved in D$_2$O and then analyzed by NMR spectroscopy. The aqueous solutions obtained in Example 12 were lyophilized, dissolved in D$_2$O, and then analyzed by NMR spectroscopy. The NMR spectrums are represented in FIGS. 10 and 11. As shown in FIG. 11, in the case of the micelle solution obtained in Example 12, the peak (appearing at around 7 ppm) corresponding to H in the aromatic ring of diclofenac disappears completely and only the peak related to polyethyleneglycol is observed. This shows that there is incorporation of diclofenac into the block copolymer. To the contrary, as shown in FIG. 12, both peaks corresponding to diclofenac and polyethyleneglycol are observed in the case of the micelle solution obtained in Comparative Example 1, which shows that diclofenac is not incorporated into the non-charged block copolymer.

Experiment 4: Confirmation on whether a Drug-Block Copolymer Complex is Formed

Figure 13:
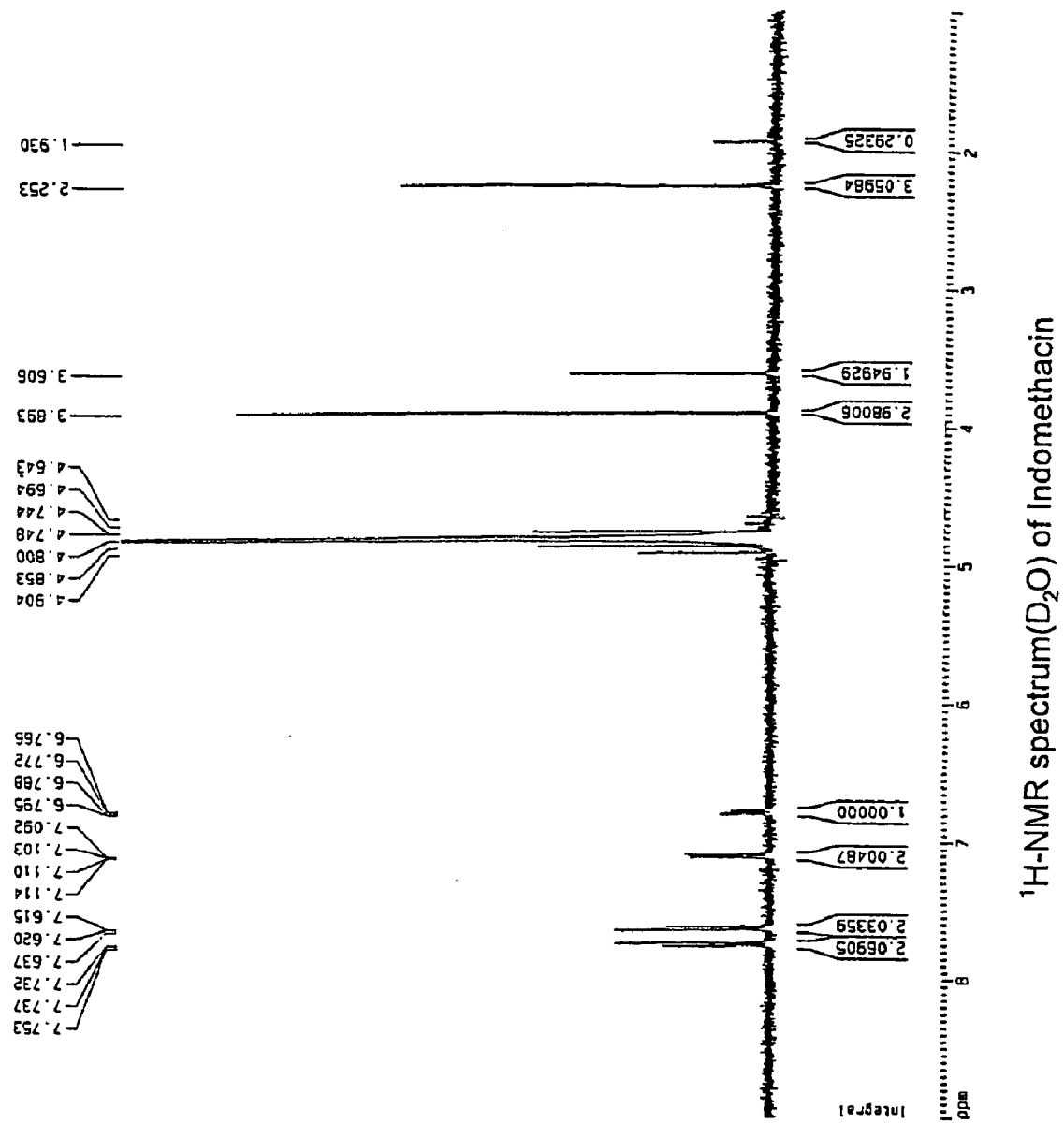
FIG. 13 is an ¹H-NMR(D₂O) spectrum of indomethacin.
Figure 14:
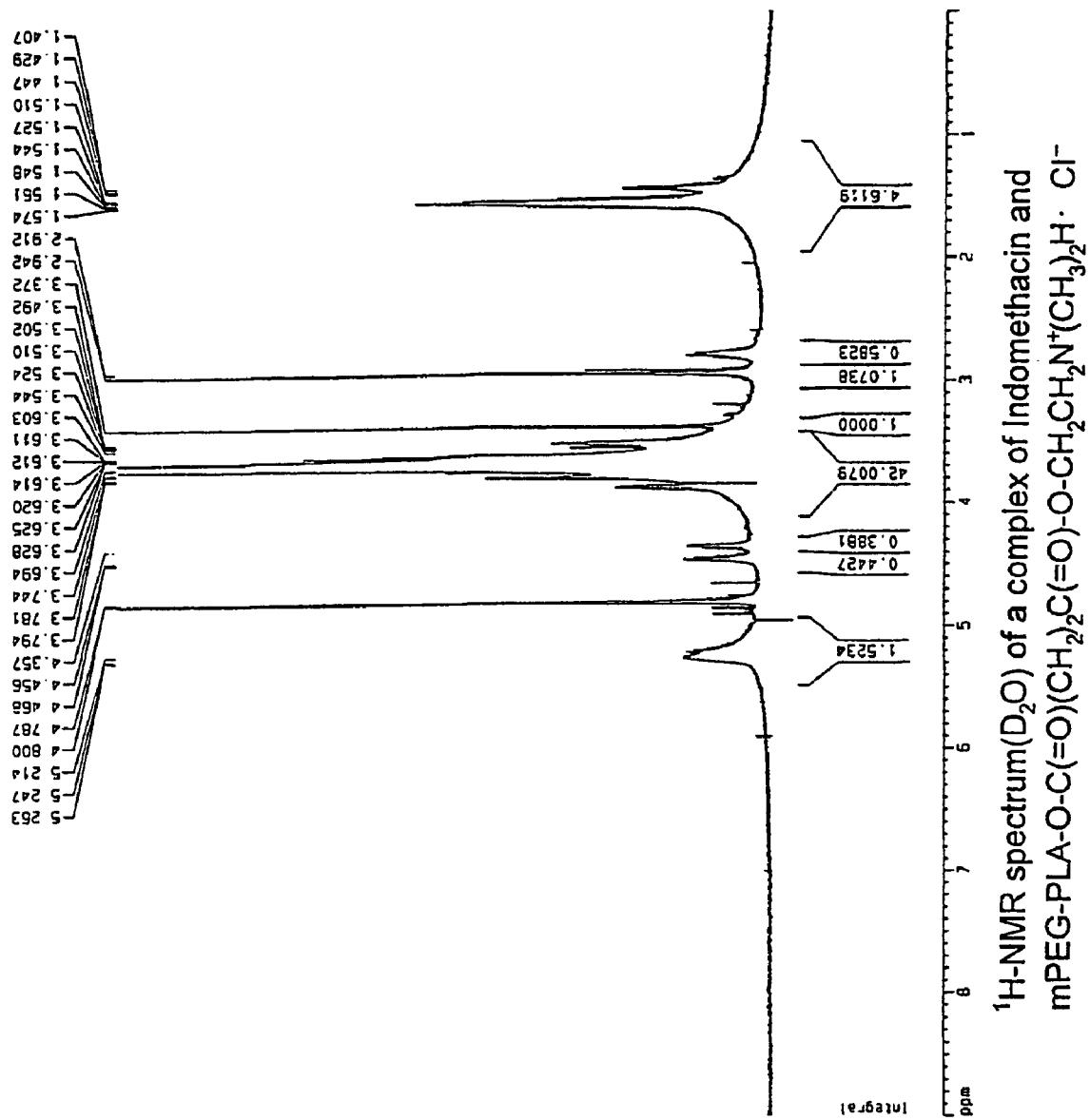
FIG. 14 is an ¹H-NMR(D₂O) spectrum of a complex of indomethacin and mPEG-PLA-O—C(=O)(CH₂)₂C(=O)—O—CH₂CH₂N⁺(CH₃)₂H.Cl⁻.

Indomethacin was dissolved in D$_2$O and then analyzed by NMR spectroscopy. The aqueous solution obtained in Example 13 was lyophilized, dissolved in D$_2$O, and then analyzed by NMR spectroscopy. The NMR spectrums are represented in FIGS. 13 and 14. As shown in FIG. 14, in the case of the micelle solution obtained in Example 13, the peak (appearing at around 7 ppm) corresponding to H in the aromatic ring of indomethacin sodium salt disappears completely and only the peak related to polyethyleneglycol is observed. This shows that there is incorporation of indomethacin into the block copolymer.

It is to be understood that the above-described embodiments are only illustrative of the applications of the principles of the present invention. Numerous modifications and alternative embodiments can be derived without departing from the spirit and scope of the present invention and the appended claims are intended to cover such modifications and arrangements. Thus, while the present invention has been shown in the drawings and fully described above with particularity and detail in connection with what is presently deemed to be the most practical and preferred embodiment(s) of the invention, it will be apparent to those of ordinary skill in the art that numerous modifications can be made without departing from the principles and concepts of the invention as set forth in the claims.

The invention claimed is:

1. A block copolymer having the formula:

wherein X is —C(═O)—(CH$_2$)$_2$—(C═O)—O—CH$_2$CH$_2$—Y or —C(═O)CHR$^1$Y; wherein R$^1$ is H, a methyl, benzyl, 2-methylpropyl or 1-methylpropyl group; Y is —NH$_3^+$, —NRH$_2^+$, —NR$_2$H$^+$, or —NR$_3^+$ wherein R is a methyl, ethyl or 2-hydroxyethyl group; and z denotes an integer from 0 to 6; M represents an anion; A is a biocompatible hydrophilic polymer; B is a biodegradable hydrophobic polymer; and L represents a linker selected from the group consisting of —O—, —NH—, —S— and —COO—.

2. The block copolymer of claim 1 wherein the number average molecular weight of each A and B is within the range of 100 to 100,000 Daltons.

3. The block copolymer of claim 1 wherein M is OH$^-$, Cl$^-$, Br$^-$, I$^-$, HSO$_4^-$, HCO$_3^-$ or NO$_3^-$.

4. A block copolymer having the formula:

wherein X is —C(═O)—(CH$_2$)$_2$—(C═O)—O—CH$_2$CH$_2$—Y or —C(═O)CHR$^1$Y; wherein R$^1$ is H, a methyl, benzyl, 2-methylpropyl or 1- methylpropyl group, Y is —NH$_3^+$, —NRH$_2^+$, —NR$_2$H$^+$, or —NR$_3^+$ wherein R is a methyl, ethyl or 2-hydroxyethyl group, and z denotes an integer from 0 to 6; M represents an anion; A$^1$ is a biocompatible hydrophilic polymer; B is a biodegradable hydrophobic polymer; L represents a linker selected from the group consisting of —O—, —NH—, —S— and —COO—; wherein said A$^1$ is a member selected from the group consisting of polyalkyleneglycol, polyalkyleneoxide, polyvinylpyrrolidone, polysaccharide, polyacrylamide, polymethacrylamide, polyvinylalcohol and derivatives thereof and said B is a biodegradable polyester.

5. The block copolymer of claim 4 wherein the number average molecular weight of each A$^1$ and B are within the range of 100 to 100,000 Daltons.

6. The block copolymer of claim 4 wherein M is OH$^-$, Cl$^-$, Br$^-$, I$^-$, HSO$_4^-$, HCO$_3^-$ or NO$_3^-$.

7. A block copolymer having the formula:

wherein X is —C(═O)—(CH$_2$)$_2$—(C═O)—O—CH$_2$CH$_2$—Y or —C(═O)CHR$^1$Y: wherein R$^1$ is H, a methyl, benzyl, 2-methylpropyl or 1- methylpropyl group, Y is —NH$_3^+$, —NRH$_2^+$, —NR$_2$H$^+$, or —NR$_3^+$ wherein R is a methyl, ethyl or 2-hydroxyethyl group: and z denotes an integer from 0 to 6; M represents OH$^-$ an anion, A$^2$ is a biocompatible hydrophilic polymer; B$^1$ is a biodegradable hydrophobic polymer; L represents a linker selected from the group consisting of —O—, —NH—, —S— and —COO—; wherein said A$^2$ is a member selected from the group consisting of polyalkyleneglycol, polyalkyleneoxide, polyvinylpyrrolidone, polysaccharide, polyacrylamide, polymethacrylamide, polyvinylalcohol and derivatives thereof and said B$^1$ is a biodegradable polyester synthesized from monomers selected from the group consisting of D,L-lactide, D-lactide, L-lactide, D,L-lactic acid, D-lactic acid, L-lactic acid, glycolide, glycolic acid, ε-caprolactone, ε-hydroxy hexanoic acid and copolymers thereof.

8. The block copolymer of claim 7 wherein the number average molecular weight of both A$^2$ and B$^1$ are within the range of 100 to 100,000 Daltons.

9. The block copolymer of claim 7 wherein M is OH$^-$, Cl$^-$, Br$^-$, I$^-$, HSO$_4^-$, HCO$_3^-$ or NO$_3^-$.

10. A block copolymer having the formula:

wherein X is —C(═O)—(CH$_2$)$_2$—(C═O)—O—CH$_2$CH$_2$—Y or —C(═O)CHR$^1$Y; wherein R$^1$ is H, a methyl, benzyl, 2-methylpropyl or 1- methylpropyl group, Y is —NH$_3^+$, —NRH$_2^+$, —NR$_2$H$^+$, or —NR$_3^+$ wherein R is a methyl, ethyl or 2-hydroxyethyl group, and z denotes an integer from 0 to 6; M represents an anion; A$^3$ is a biocompatible hydrophilic polymer; B is a biodegradable hydrophobic polymer; L represents a linker selected from the group consisting of —O—, —NH—, —S— and —COO—; and wherein said A$^3$ is a degradable derivative prepared according to the following reaction scheme:

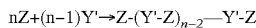

wherein Z represents a water-soluble polymer having a molecular weight of up to 5,000 Daltons, Y' represents HOOC—(CH$_2$)$_m$—COOH or O═C═N—(CH$_2$)$_m$—N═C═O wherein m is an integer from 0 to 10 and n is an integer from 2 to 100.

11. The block copolymer of claim 10 wherein the number average molecular weight of both A$^3$ and B are within the range of 100 to 100,000 Daltons.

12. The block copolymer of claim 10 wherein M is OH$^-$, Cl$^-$, Br$^-$, I$^-$, HSO$_4^-$, HCO$_3^-$ or NO$_3^-$.

13. A composition comprising the block copolymer of claim 1 and a negatively charged drug wherein said negatively charged drug combines with one or more of said block copolymers and forms a drug-block copolymer complex via electrostatic forces.

14. A composition comprising the block copolymer of claim 4 and a negatively charged drug wherein said negatively charged drug combines with one or more of said block copolymers and forms a drug-block copolymer complex via electrostatic forces.

15. A composition comprising the block copolymer of claim 7 and a negatively charged drug wherein said negatively charged drug combines with one or more of said block copolymers and forms a drug-block copolymer complex via electrostatic forces.

16. A composition comprising the block copolymer of claim 10 and a negatively charged drug wherein said negatively charged drug combines with one or more of said block copolymers and forms a drug-block copolymer complex via electrostatic forces.

* * * * *